United States Patent
Komatsu et al.

(10) Patent No.: US 9,180,161 B2
(45) Date of Patent: Nov. 10, 2015

(54) CAR PEPTIDE FOR HOMING, DIAGNOSIS AND TARGETED THERAPY FOR PULMONARY AND FIBROTIC DISORDERS

(75) Inventors: Masanobu Komatsu, Orlando, FL (US); David Marshall Mann, San Diego, CA (US); Erkki Ruoslahti, Busilton, CA (US)

(73) Assignees: Sanford Burnham Prebys Medical Discovery Institute, La Jolla, CA (US); Vascular BioSciences, San Diego, CA (US)

( * ) Notice: Subject to any disclaimer, the term of this patent is extended or adjusted under 35 U.S.C. 154(b) by 0 days.

(21) Appl. No.: 13/581,457

(22) PCT Filed: Feb. 28, 2011

(86) PCT No.: PCT/US2011/026535
§ 371 (c)(1),
(2), (4) Date: Feb. 26, 2013

(87) PCT Pub. No.: WO2011/106788
PCT Pub. Date: Sep. 1, 2011

(65) Prior Publication Data
US 2013/0196896 A1 Aug. 1, 2013

Related U.S. Application Data

(60) Provisional application No. 61/308,826, filed on Feb. 26, 2010.

(51) Int. Cl.
*A61K 38/08* (2006.01)
*C07K 7/06* (2006.01)
*A61K 45/06* (2006.01)
*A61K 47/48* (2006.01)
*A61K 38/00* (2006.01)

(52) U.S. Cl.
CPC ............... *A61K 38/08* (2013.01); *A61K 45/06* (2013.01); *A61K 47/48246* (2013.01); *C07K 7/06* (2013.01); *A61K 38/00* (2013.01)

(58) Field of Classification Search
CPC ....... A61K 38/00; A61K 45/06; A61K 38/08; A61K 47/48246; C07K 7/06
See application file for complete search history.

(56) References Cited

U.S. PATENT DOCUMENTS

2008/0213377 A1* 9/2008 Bhatia et al. ............... 424/489
2009/0036349 A1* 2/2009 Ruoslahti et al. ............ 514/2

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Harata et al, CD19-targeting liposomes containing imatinib efficiently kill Philadelphia chromosome—positive acute lymphoblastic leukemia cells, Blood, 2004, 104, pp. 1442-1449.*
Liposomes—Types of Nanoparticles—Lipids and Drug Delivery, from http://biotech.about.com/od/glossary/g/Liposomes.htm?p=1, p. 1, accessed Nov. 25, 2013.*
Insulin-homo sapiens, from http://www.ncbi.nlm.nih.gov/protein/AAA59172.1, p. 1, accessed May 12, 2014.*
Hypothetical protein Mefer_1314, from http://www.genome.jp/dbget-bin/www_bget?refseq:YP_003128623, p. 1, accessed Jun. 3, 2014.*
Chemotherapy Principles, from American Cancer Society, 2013, pp. 1-29.*
Jarvinen et al., Molecular Changes in the Vasculature of Injured Tissues, (2007) American Journal of Pathology 171 (2):702-711.

* cited by examiner

*Primary Examiner* — Julie Ha
*Assistant Examiner* — Li Ni Komatsu
(74) *Attorney, Agent, or Firm* — Lewis Kohn & Walker LLP; David M. Kohn; Kari Moyer-Henry

(57) ABSTRACT

Disclosed are compositions and methods useful for delivering targeted therapies for pulmonary diseases, fibrotic disorders and cancer. The compositions and methods are based on peptide sequences that selectively bind to and home to diseased tissue and enable targeted therapies to effect a beneficial therapeutic result. The disclosed targeting is useful for delivering therapeutic and detectable agents to diseased tissue in an animal.

2 Claims, 44 Drawing Sheets

Control vs. MCT – CAR-FITC stain

Control  MCT (CAR-FITC)

Control vs. MCT – Alveoli- H&E

CAR vs CARM Staining in SU 5146/hypoxia PAH Rat Model

LUNG

CAR

CAR-M

PULMONARY ARTERY

CAR　　　　　　　　CAR-M

PULMONARY ARTERY

CAR                   CAR-M

PULMONARY ARTERY

CAR                   CAR-M

PULMONARY ARTERY

CAR     CAR-M

PULMONARY ARTERY

CAR

CAR-M

LIVER

SPLEEN

CAR staining in Bleomycin Mouse Model of Pulmonary Fibrosis 14 d CAR
Fibrosis 14 d CAR
Adjacent to
fibrosis — Interstitial staining
— Inflammatory cells 14 d VCAM
Mild Fibrosis Very little specific staining 14 d VCAM
Spared area

|  | Baseline | CARK 3mg/kg + fasudil 1mg/kg |
|---|---|---|
| RVSP (mmHg) | 89.9 | 66.9 |
| SAP (mmHg) | 134.9 | 146.1 |

| | Baseline | CARK 3mg/kg + fasudil 1mg/kg-1 | CARK 3mg/kg + fasudil 1mg/kg-2 |
|---|---|---|---|
| RVSP (mmHg) | 84.6 | 69.6 | 87.9→63.6 |
| LVSP (mmHg) | 140.6 | 123.9 | 136.9→128.9 |

CAR PEPTIDE FOR HOMING, DIAGNOSIS AND TARGETED THERAPY FOR PULMONARY AND FIBROTIC DISORDERS

CROSS REFERENCES

This application is a United States National Stage Application claiming priority under 35 U.S.C. 371 from International Patent Application No. PCT/US2011/26535 filed Feb. 28, 2011, which claims the benefit of priority from U.S. Provisional Patent Application No. 61/308,826, filed Feb. 26, 2010, the entire contents of which are herein incorporated by reference.

GOVERNMENT SUPPORT STATEMENT

This invention was made with government support under grant 1 R41 HL088771 from the National Heart Lung Blood Institute of the NIH. The government has certain rights in the invention.

FIELD OF THE INVENTION

The present invention relates generally to the field of targeted therapies, more specifically, to therapies that selectively target diseased pulmonary and fibrotic tissue.

BACKGROUND OF THE INVENTION

Tissue regeneration, inflammation and tumors induce the growth of new blood vessels from pre-existing ones. This process, angiogenesis, is a vital requirement for wound healing as the formation of new blood vessels allows a variety of mediators, nutrients, and oxygen to reach the healing tissue (Martin 1997, Singer & Clark 1999, Falanga 2006, Folkman 2006). Newly formed blood vessels differ in structure from pre-existing vasculature. Such differences have been extensively characterized by comparing tumor vasculature to normal vessels (Ruoslahti, 2002). Angiogenic vessels in non-malignant tissues and in pre-malignant lesions share markers with tumor vessels (Gerlag et al, 2001), but distinct markers also exist (Hoffman et al., 2003; Joyce et al., 2003).

Regarding tissue injuries, substantive basic science and clinical research have been conducted to evaluate the mechanisms of wound healing, the efficacy of various modalities for treatment of wounds, and the best methods for diagnosing wound infection. Tissue injuries caused by trauma, medical procedures, and inflammation are a major medical problem. Systemic medication is available for most major medical conditions, but therapeutic options in promoting tissue regeneration are largely limited to local intervention. As deep injuries and multiple sites of injury often limit the usefulness of local treatment, systemic approaches to tissue regeneration are valuable.

A major problem limiting tissue regeneration is scar formation. The response to tissue injury in adult mammals seems to be mainly focused on quick sealing on the injury. Fibroblast (astrocyte, smooth muscle cell) proliferation and enhanced extracellular matrix production are the main element of the sear formation, and the sear prevents tissue regeneration. In contrast, fetal tissues heal by a process that restores the original tissue architecture with no scarring. Transforming growth factor.beta. (TGF-.beta.) is a major factor responsible for impaired tissue regeneration, scar formation and fibrosis (Werner and Grose 2002; Brunner and Blakytny 2004; Leask and Abraham 2004).

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life. For decades, researchers have examined avenues to increase targeted specificity of therapeutics against only the disease, thereby preserving normal cellular integrity.

One manner by which therapeutic specificity may be increased is by targeting diseases at the cellular level. More specifically, therapeutics may be enhanced by interacting directly with those components at the level of the cell surface or membrane. These components include, among others, laminin, collagen, fibronectin and other proteoglycans. Proteoglycans are proteins classified by a posttranslational attachment of polysaccharide glycosaminoglycan (GAG) moieties each comprised of repeating disaccharide units. One monosaccharide of the disaccharide repeat is an amino sugar with D-glucosamine or galactosamine, and the other unit is typically, but not always, a uronic acid residue of either D-glucuronic acid or iduronic acid. Both units are variably N- and O-sulfated, which adds to the heterogeneity of these complex macromolecules. They can be found associated with both the extracellular matrix and plasma membranes. The most common GAG structures are dermatan sulfate (DS), chondroitin sulfate (CS), heparan sulfate (HS), keratan sulfate (KS), hyaluronic acid (HA), and heparin; representative structures for each disaccharide are shown below.

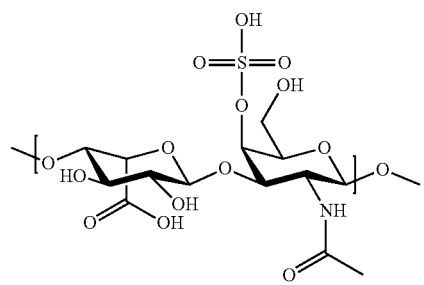

Dermatan sulfate

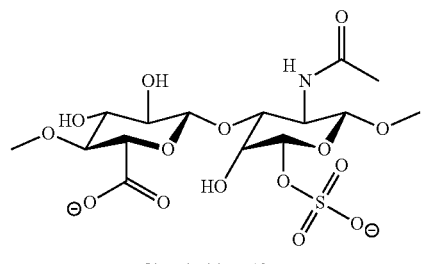

Chondroitin sulfate

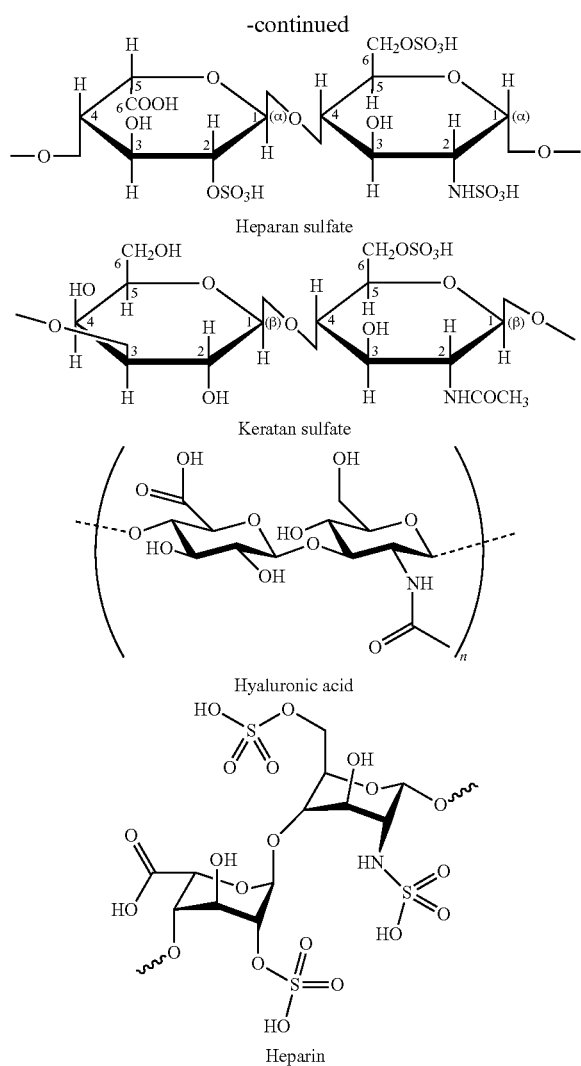

These unbranched sulfated GAGs are defined by the repeating disaccharide units that comprise their chains, by their specific sites of sulfation, and by their susceptibility to bacterial enzymes known to cleave distinct GAG linkages. All have various degrees of sulfation which result in a high density of negative charge. Proteoglycans can be modified by more than one type of GAG and have a diversity of functions, including roles in cellular adhesion, differentiation, and growth. In addition, cell surface proteoglycans are known to act as cellular receptors for some bacteria and several animal viruses, including; foot-and-mouth disease type O virus, HSV types 1 and 2 and dengue virus. Accordingly, it would be advantageous from a therapeutic perspective to design agents which may be used at the cell surface level.

A major function of cell surface proteoglycans is in cell adhesion and migration, dynamic processes that are mediated through interactions between the proteoglycan GAG chains and extracellular matrix (ECM) components, such as laminin, collagen, and fibronectin. Proteoglycans also occur as integral components of basement membranes in most mammalian tissues. Interactions of these macromolecules with other ECM constituents contribute to the general architecture and permeability properties of the basement membrane, and thus these GAGs play a structural role. Proteoglycans and GAGs play a critical role in the pathophysiology of basement membrane-related diseases, including diabetes, atherosclerosis, and metastasis. In addition, cell-specific growth factors and enzymes are immobilized in the ECM and at the cell surface are bound to GAGs. As such, GAGs localize proteins and enzymes at their site of action to facilitate their physiological functions and in some cases prevent their proteolytic degradation. Proteoglycans and GAGs have been shown to regulate protein secretion and gene expression in certain tissues by mechanisms involving both membrane and nuclear events, including the binding of GAGs to transcription factors (Jackson, R. L. 1991). Limited information is available on the factors that regulate the expression of proteoglycans and their associated GAGs. There is a need in the art to develop cell-penetrating agents which bind to cell surface proteoglycans in order to have disease-specific efficacy.

US Patent Application Publication No. 20090036349 discloses a novel composition that selectively binds to regenerating tissue, wound sites and tumors in animals. In vivo screening of phage-displayed peptide libraries was used to probe vascular specialization. This screening method resulted in the identification of several peptides that selectively target phage to skin and tendon wounds. One peptide in particular was identified and contains the following sequence: CARSKNKDC (CAR) (SEQ ID NO:1). CAR displays homology to heparin-binding sites in various proteins, and binds to cell surface heparan sulfate and heparin. More specifically, CAR binds to glycosaminoglycan moieties in cell surface heparan sulfate proteoglycans (HSPGs) (Jarvinen and Ruoslahti 2007), and other cell-penetrating peptides have also mediated their entry into cells through binding to HSPGs (Poon and Gariépy 2007). HSPGs fine-tune mammalian physiology and orchestrate metabolism, transport, information transfer, support and regulation at the systemic level, as well as the cellular level (Bishop, Schuksz and Esko 2007). Overexpression of HSPG biosynthetic enzymes result in distinct heparan sulfate sulfation patterns (Pikas, Erikson and Kjellen 2000). The overexpression of HSPG biosynthetic enzymes have not been previously detected in a disease in which the co-administration of a cell penetrating peptide along with a bioactive agent which results in the disease-selective action of the co-administration of the peptide/agent combination.

There is a need for selectively targeting specific sites of action through co-administration of a targeting peptide with a bioactive agent in order to increase the efficacy of the combination therapy.

BRIEF DESCRIPTION OF THE DRAWINGS

FIG. 1 shows a comparison of CAR-FITC staining between control rat pulmonary cross-sections and monocrotaline (MCT) induced hypertensive pulmonary artery.

FIG. 2 shows a hematoxylin and eosin (H&E) stain of rat pulmonary artery illustrating the vascular remodeling and thicker arterial walls seen in the MCT induced hypertensive pulmonary artery as compared to control rat pulmonary artery.

FIG. 3 shows a H&E stain of rat pulmonary aveoli and arterioles showing more remodeling and alveolar macrophages in MCT rat as compared to control.

FIG. 4 shows alveolar macrophages take up the stain for CAR-FITC in the MCT rat FIGS. 5-13 depict varying distributions of CAR and the control peptide CARM in tissues from the late stage SU5146/hypoxia/normoxia exposed rats. Tissue samples were collected 2 hours after injections of FAM-labeled CAR or CARM peptide via tail vein (1 mg/300 g body weight). Low power magnification of lung tissues (FIG. 5), high power magnification of severely remodeled (Grade 4) pulmonary arterial lesions (FIGS. 6-10), low power and high power magnification photos of liver (FIG. 11), spleen (FIG. 12), kidney (FIG. 13).

Figure 19:
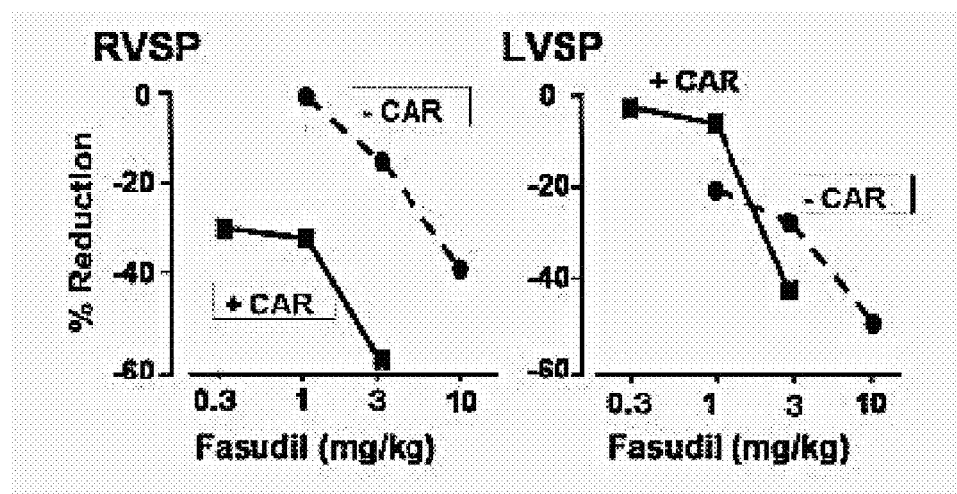

FIG. 19 shows the effects of acute administration of fasudil with (+ CAR) and without co-administration of CAR (1 mg/300 g rat) (− CAR) on right (RVSP) and left ventricle systolic pressure (LVSP). Vasodilator effects were expressed as % reduction of baseline pressure. Values are means of n=1-2 each.

Figure 20:
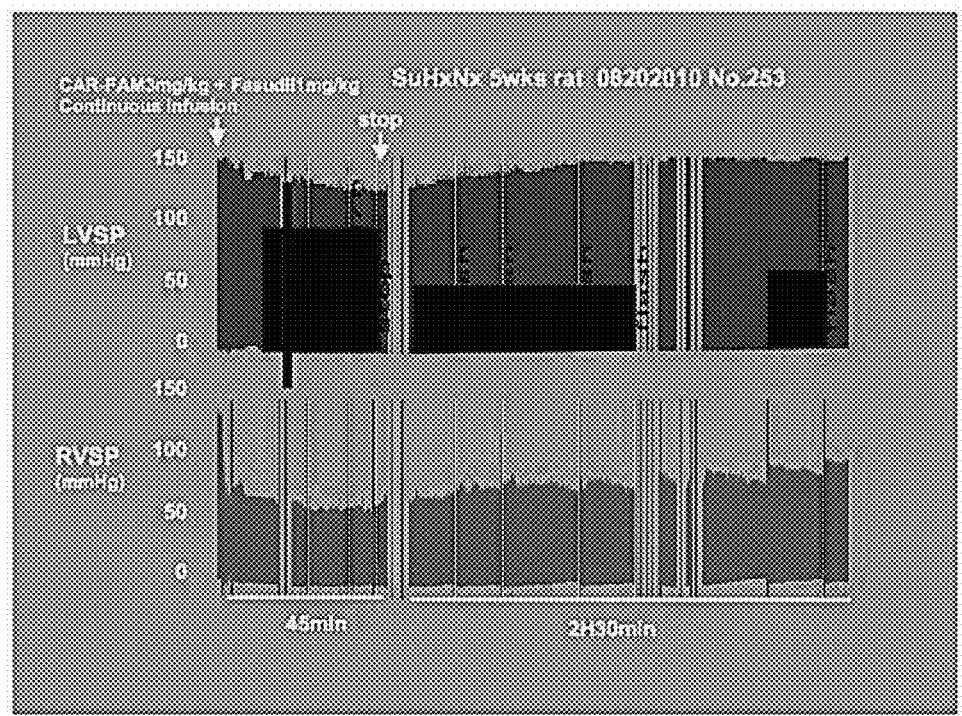

FIG. 20 shows a continuous infusion of CAR+fasudil and the effects on the RVSP and LVSP.

Figure 21:
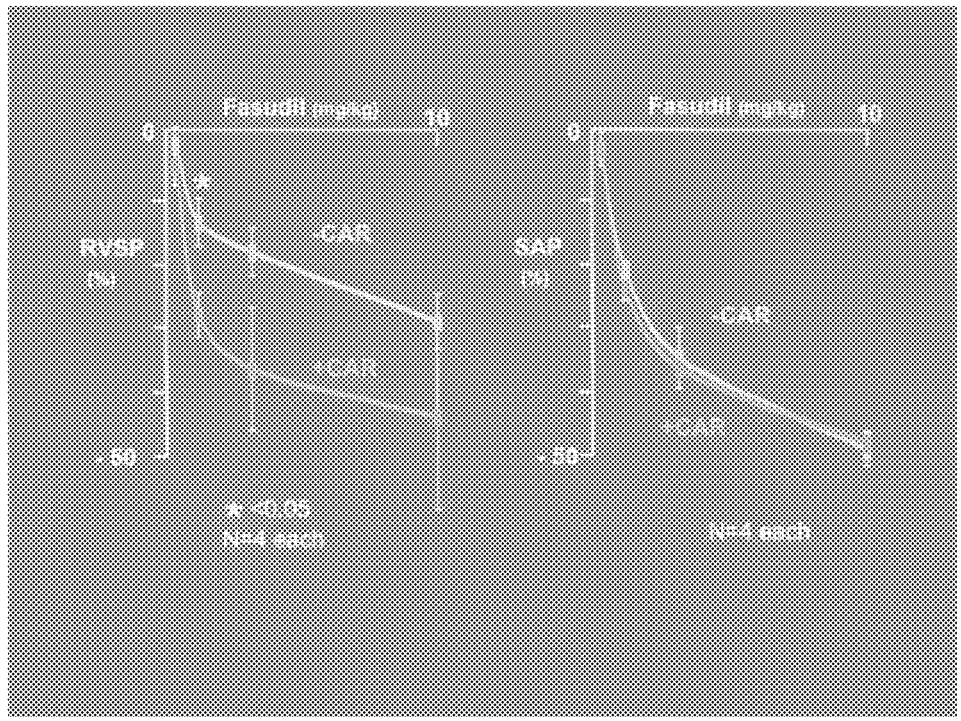

FIG. 21 shows the pulmonary selective enhancement of fasudil when co-administered with CAR in the severe occlusive PAH rat model. Fasudil dosing ranges from 1 to 10 mg/kg. RVSP and SAP were analyzed after fasudil dosing, both with and without CAR.

Figure 22:
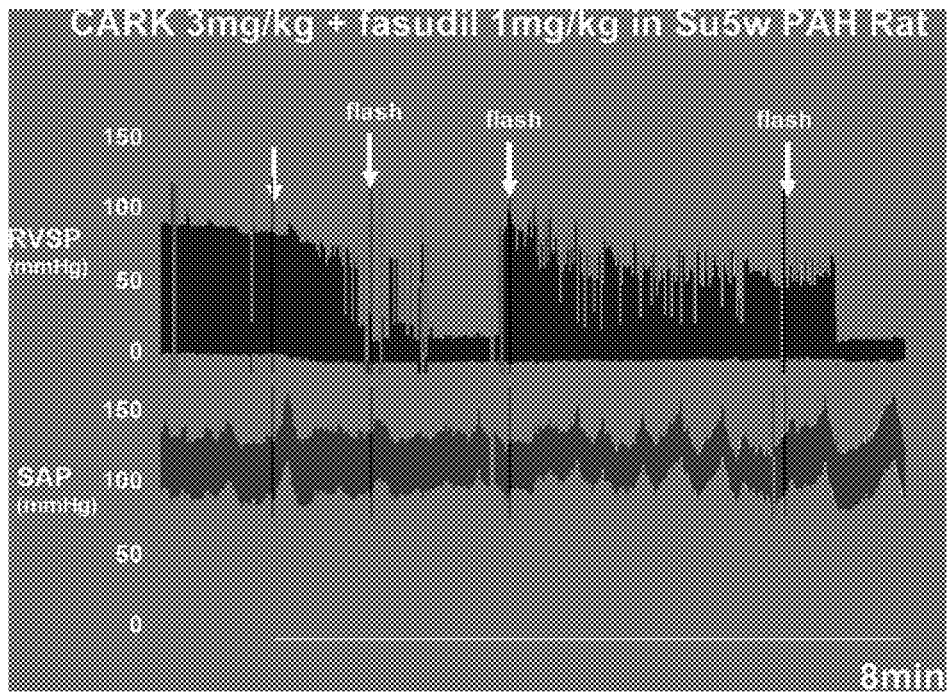

FIG. 22 shows a blood tracing experiment with fasudil co-administered with CARK. Fasudil was dosed at 1 mg/kg and CARK dosed at 3 mg/kg. Pressure measurements were observed at RVSP (mmHg) and SAP (mmHg).

Figure 23:
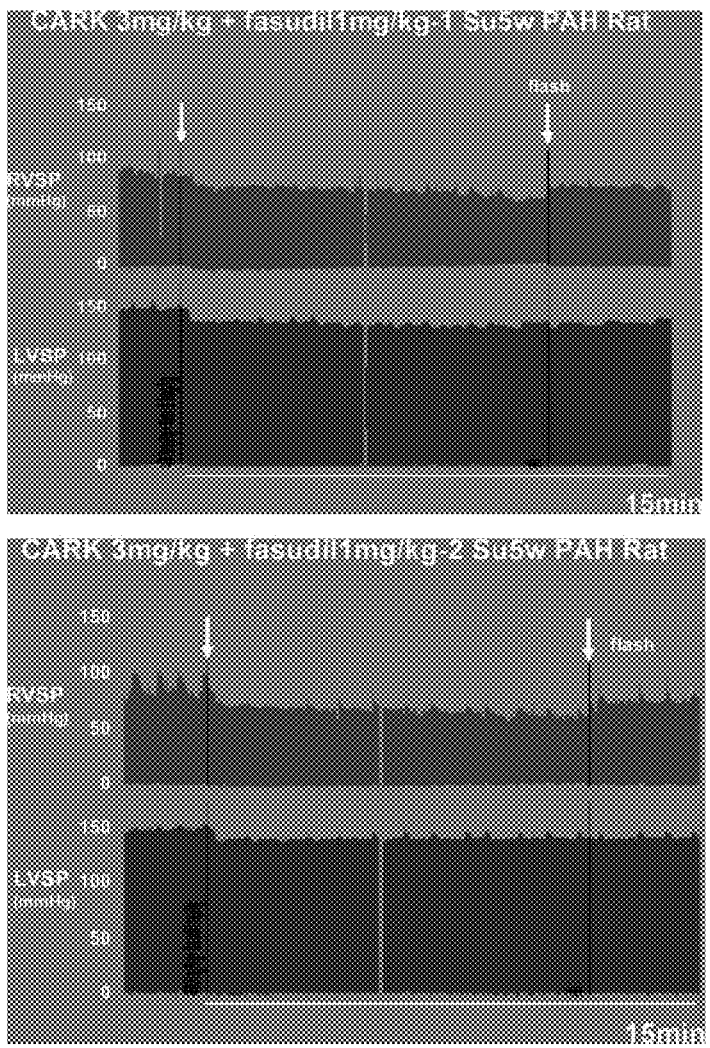

FIG. 23 shows blood tracing experiments with fasudil co-administered with CARK. Fasudil was dosed at 1 mg/kg and CARK dosed at 3 mg/kg. Pressure measurements were observed at RVSP (mmHg) and LVSP (mmHg).

Figure 24:
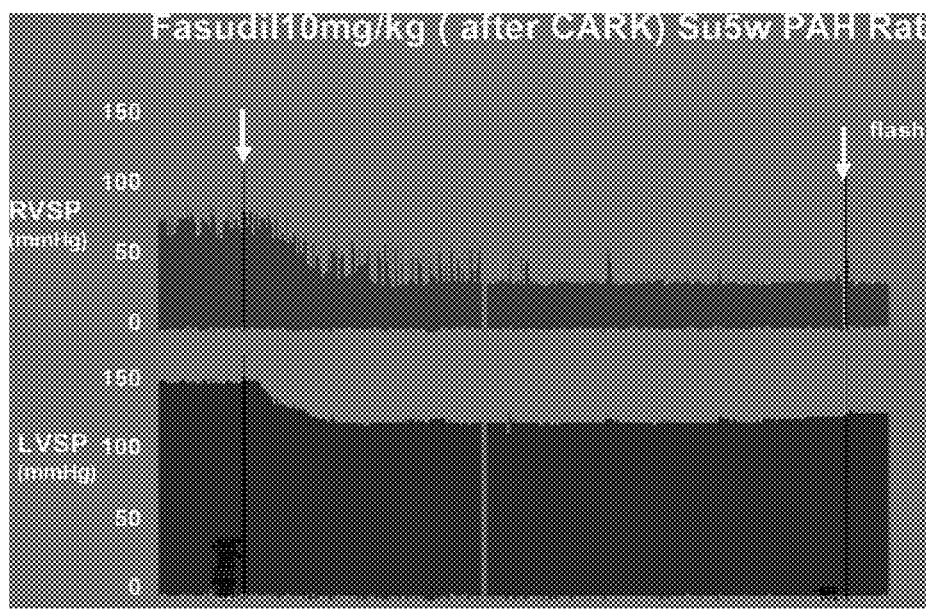

FIG. 24 shows a blood tracing experiment with fasudil administered after cessation of CARK infusion. Fasudil was dosed at 10 mg/kg. Pressure measurements were observed at RVSP (mmHg) and LVSP (mmHg).

Figure 25:
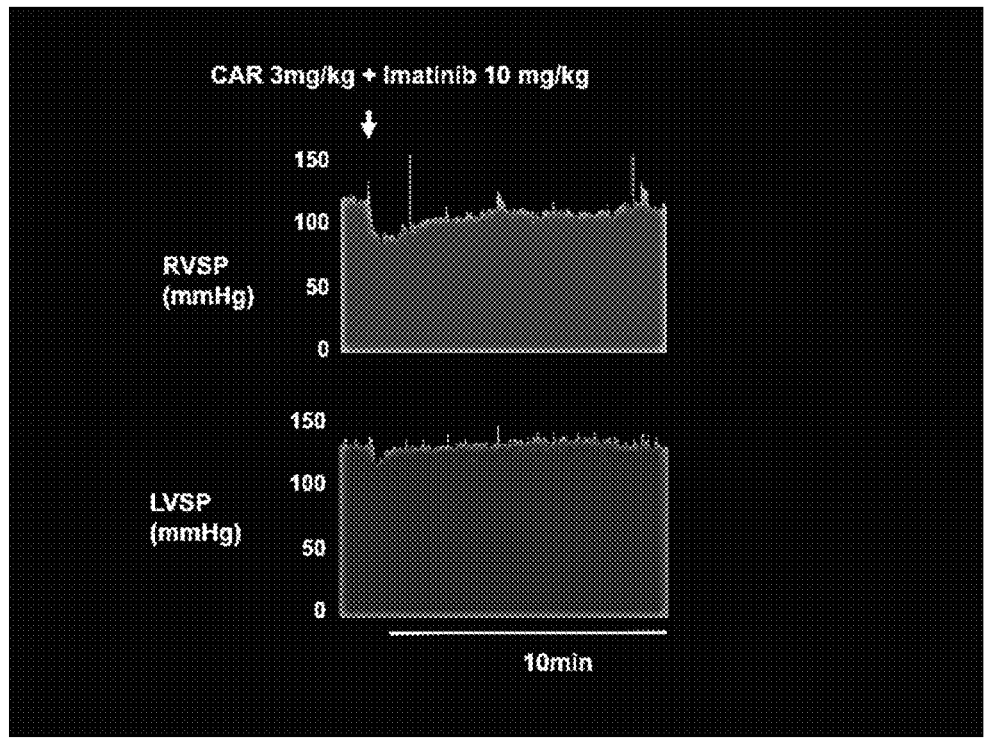

FIG. 25 shows a blood tracing experiment with imatinib co-administered with CAR. Imatinib was dosed at 10 mg/kg and CAR dosed at 3 mg/kg.

Figure 26:
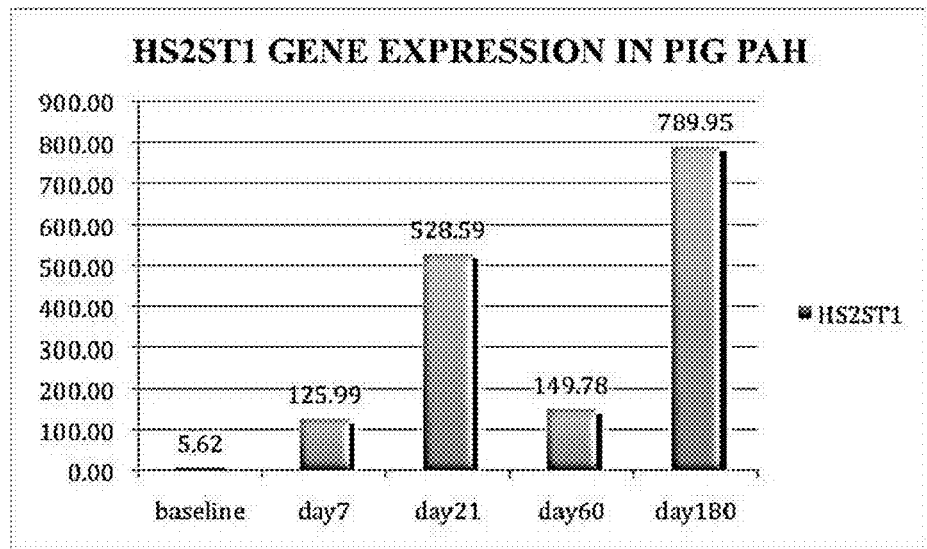

FIG. 26 shows gene expression levels of HS2ST1 (heparan sulfate 2-O-sulfotransferase 1) in the PAH model. HS2ST1 catalyzes the transfer of sulfate to the C2-position of selected hexuronic acid residues within the maturing heparan sulfate.

Figure 27:
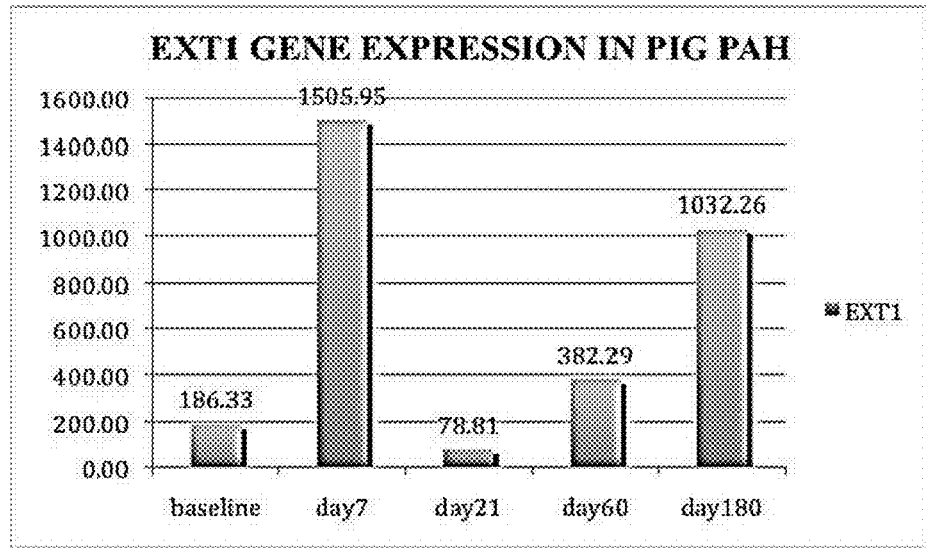

FIG. 27 shows gene expression levels of EXT1 (exostosin 1) in the PAH model. EXT1 is an endoplasmic reticulum-resident type II transmembrane glycosyltransferase involved in the chain elongation step of heparan sulfate biosynthesis.

Figure 28:
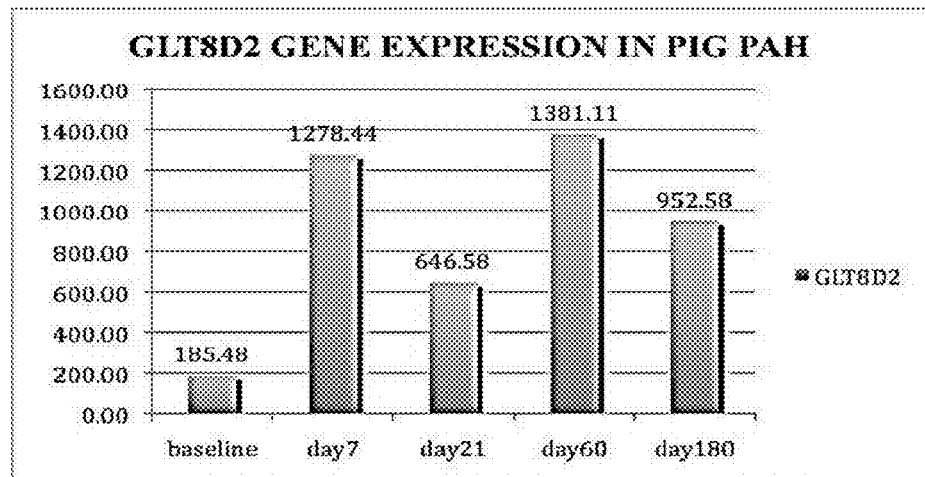

FIG. 28 shows gene expression levels of GLT8D2 (glycosyltransferase 8 domain containing 2) in the PAH model. GLT8D2 is an enzyme involved in HSPG biosynthesis.

Figure 29:
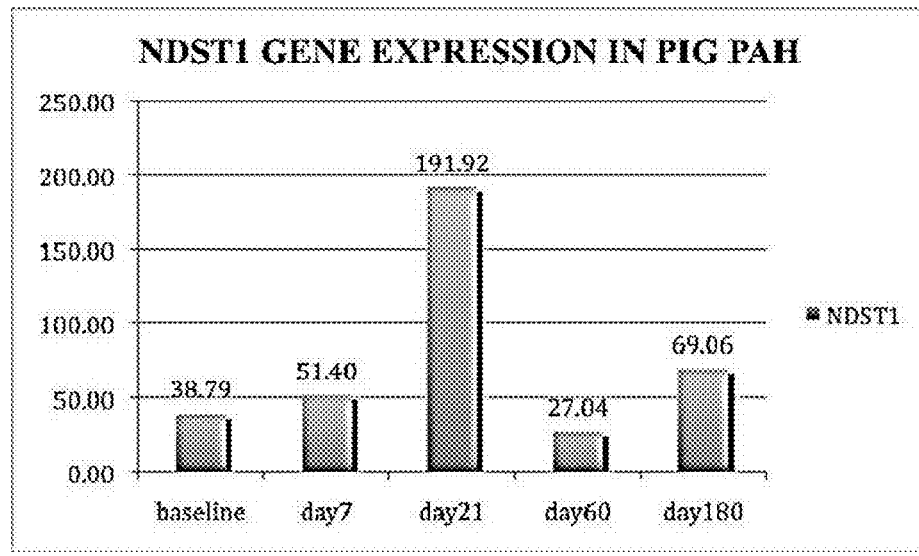

FIG. 29 shows gene expression levels of NDST1 (Heparan sulfate N-deacetylase/N-sulfotransferase) in the PAH model. NDST1 is a HSPG biosynthetic enzyme.

Figure 30:
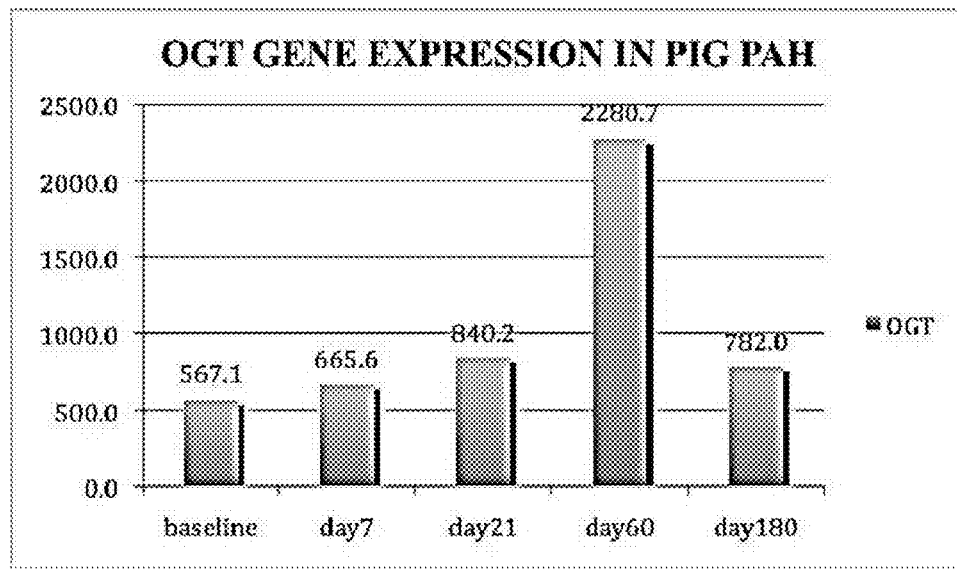

FIG. 30 shows gene expression levels of OGT (O-linked N-acetylglucosamine (O-GlcNAc) transferase) in the PAH model. OGT catalyzes the addition of a single N-acetylglucosamine in O-glycosidic linkage to serine or threonine residues of intracellular proteins including HSPGs.

Figure 31:
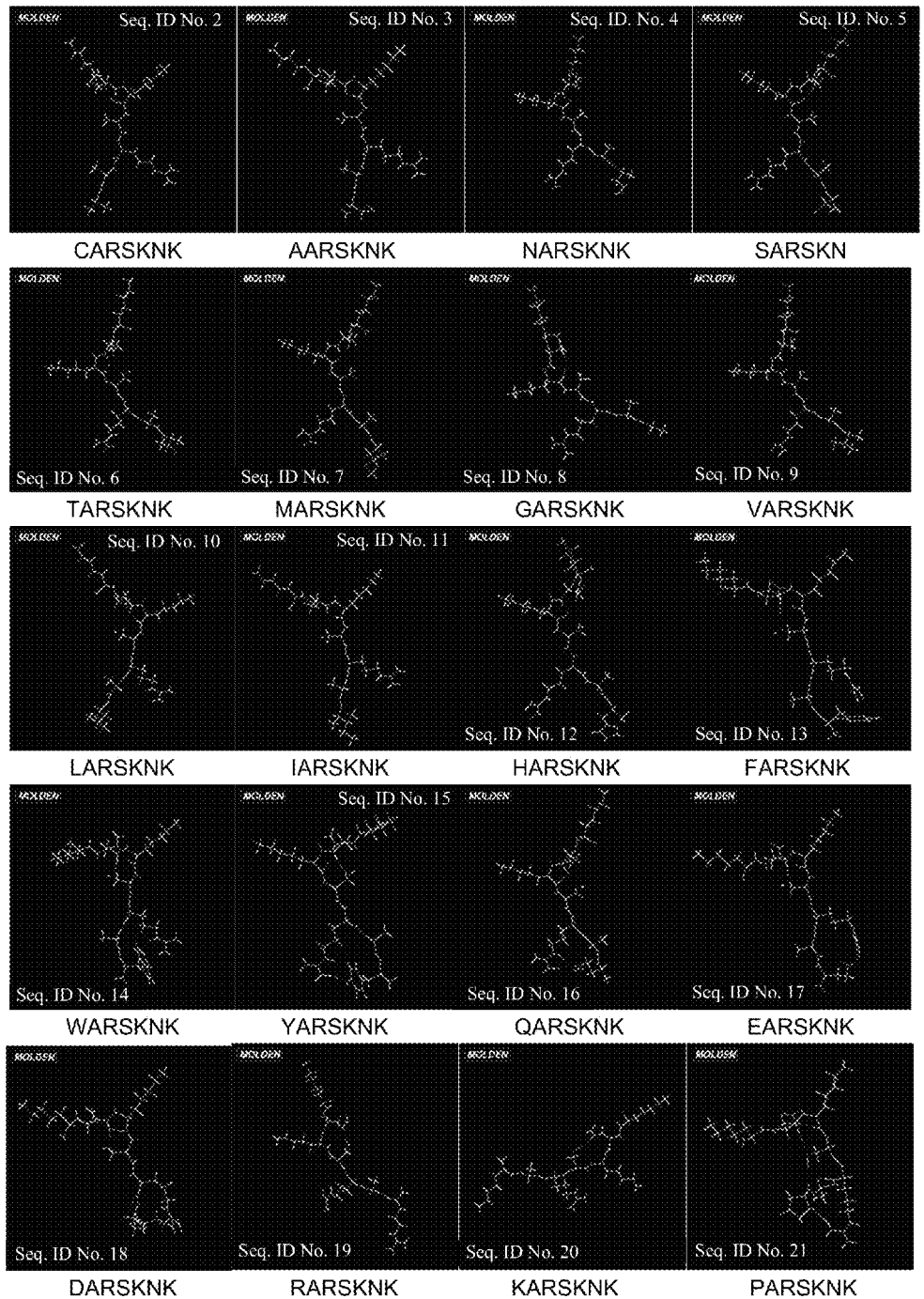

FIG. 31 shows the molecular structure of CARK (in upper left) and substitutional variants of CARK in which each of the other 19 amino acids are substituted for the N terminus cysteine (C).

Figure 32:
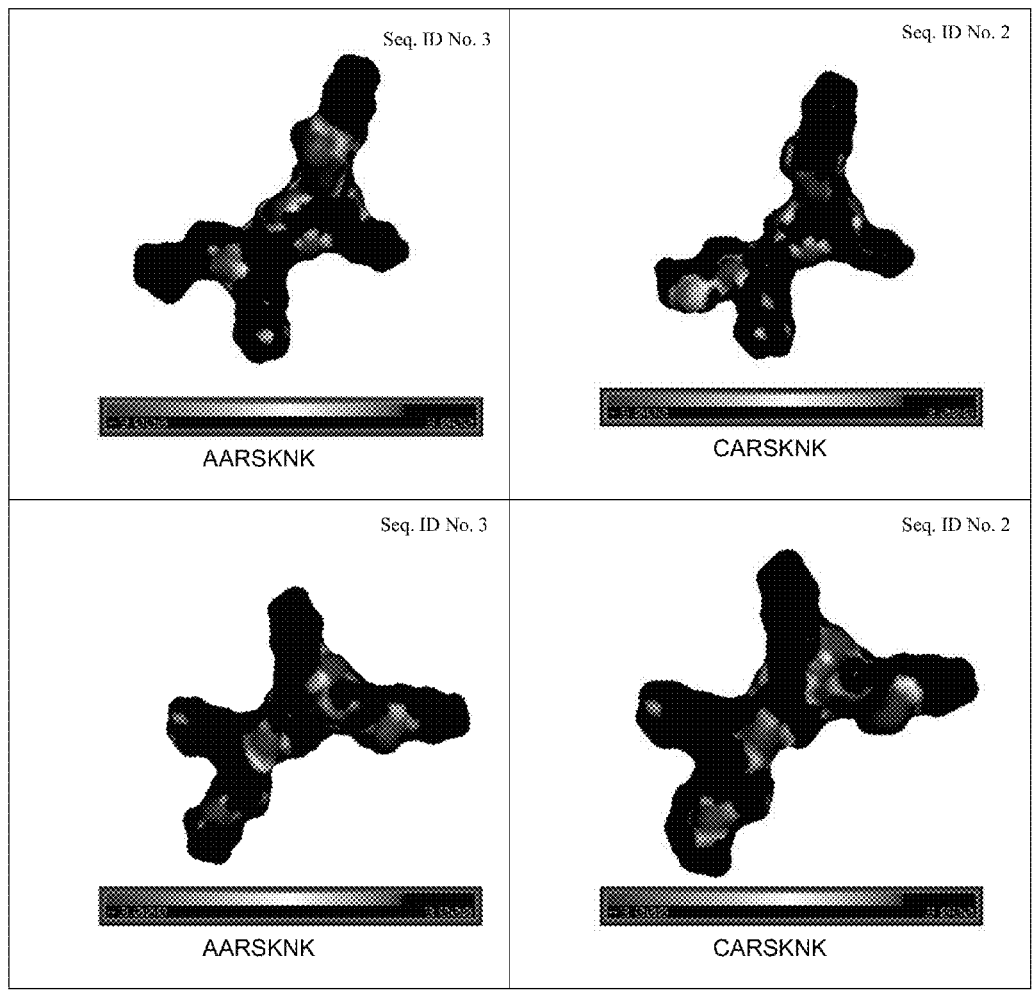

FIG. 32 shows a conformational comparison between the electrostatic potential surface structure of CARK (right images) and a substitutional variant AARSKNK (SEQ ID NO: 3) (left images) in which alanine (A) has been substituted for the N terminus cysteine (C).

Figure 33:
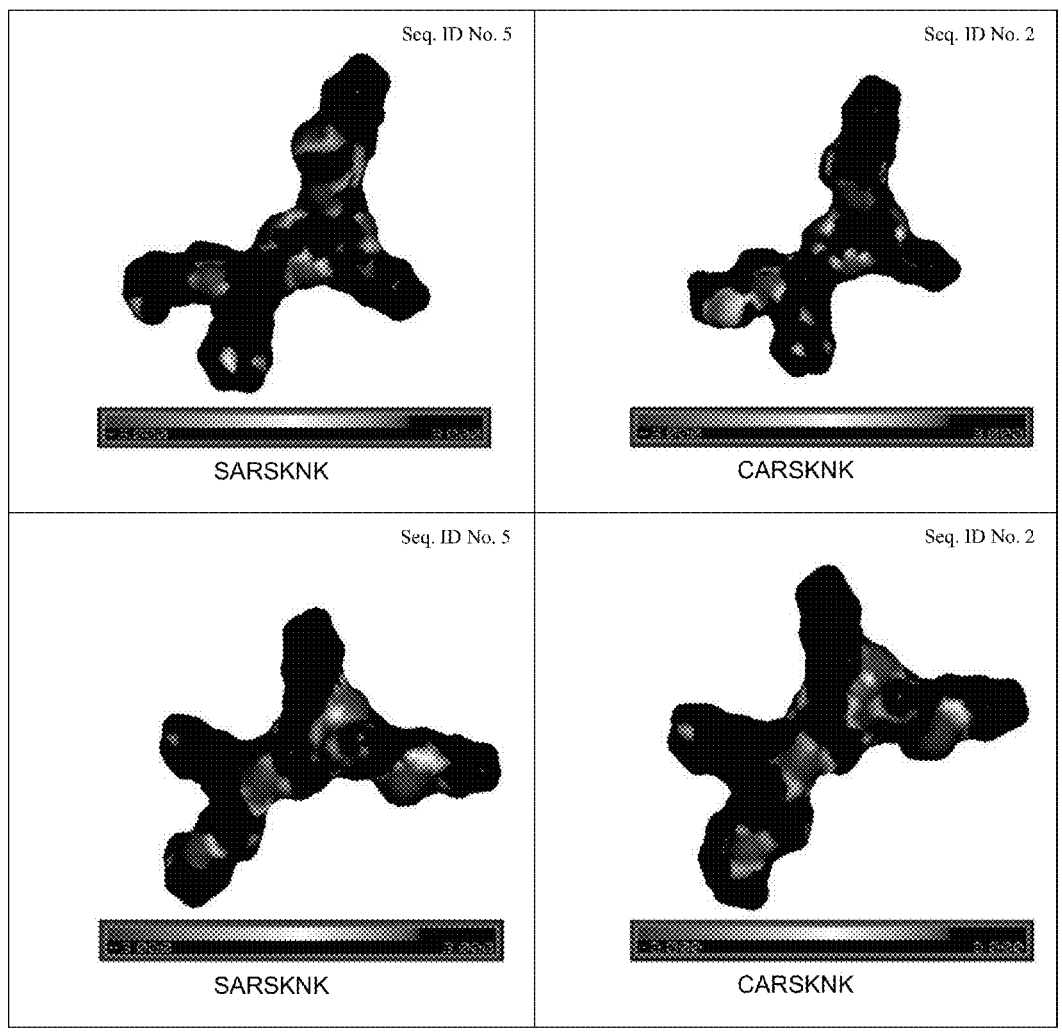

FIG. 33 shows a conformational comparison between the electrostatic potential surface structure of CARK (right images) and a substitutional variant SARSKNK (SEQ ID NO: 5) (left images) in which serine (S) has been substituted for the N terminus cysteine (C).

Figure 34:
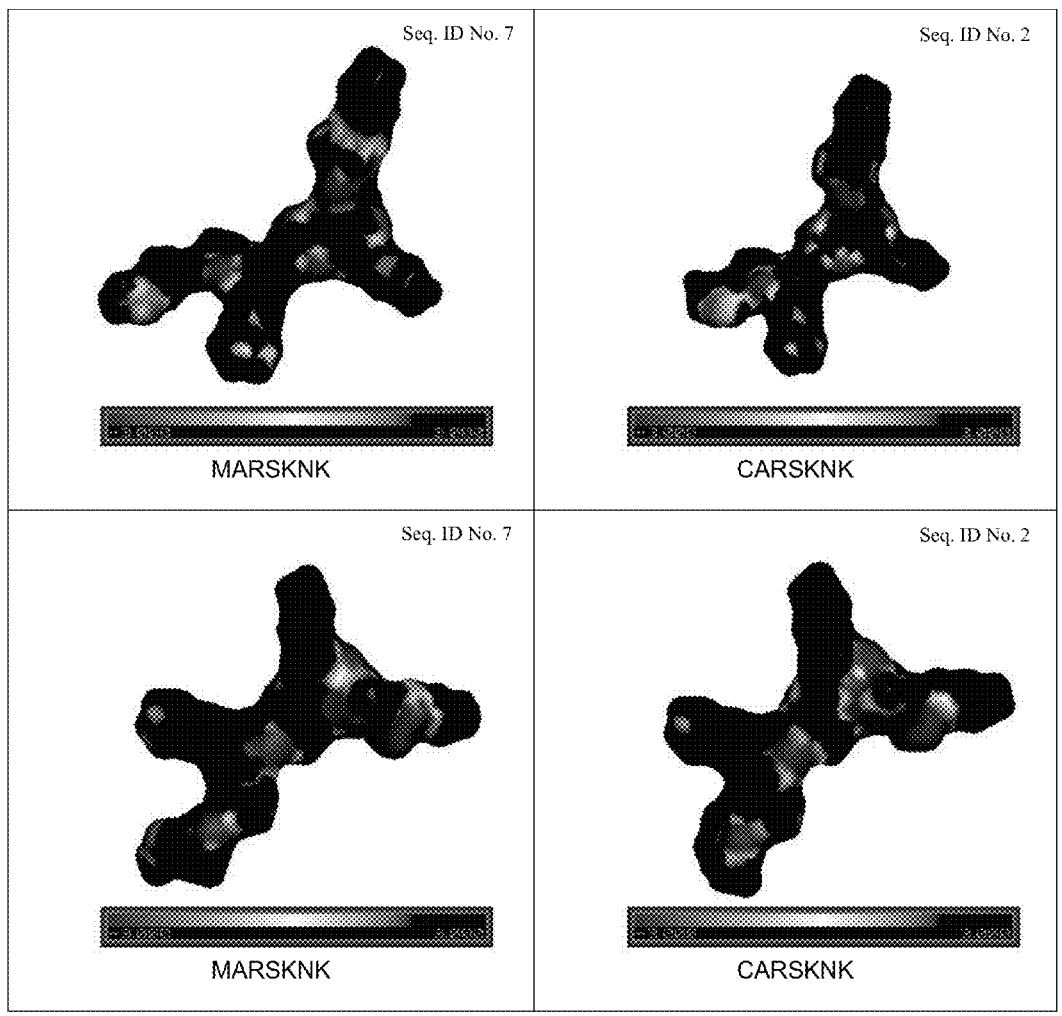

FIG. 34 shows a conformational comparison between the electrostatic potential surface structure of CARK (right images) and a substitutional variant MARSKNK (SEQ ID NO: 7) (left images) in which methionine (M) has been substituted for the N terminus cysteine (C).

Figure 35:
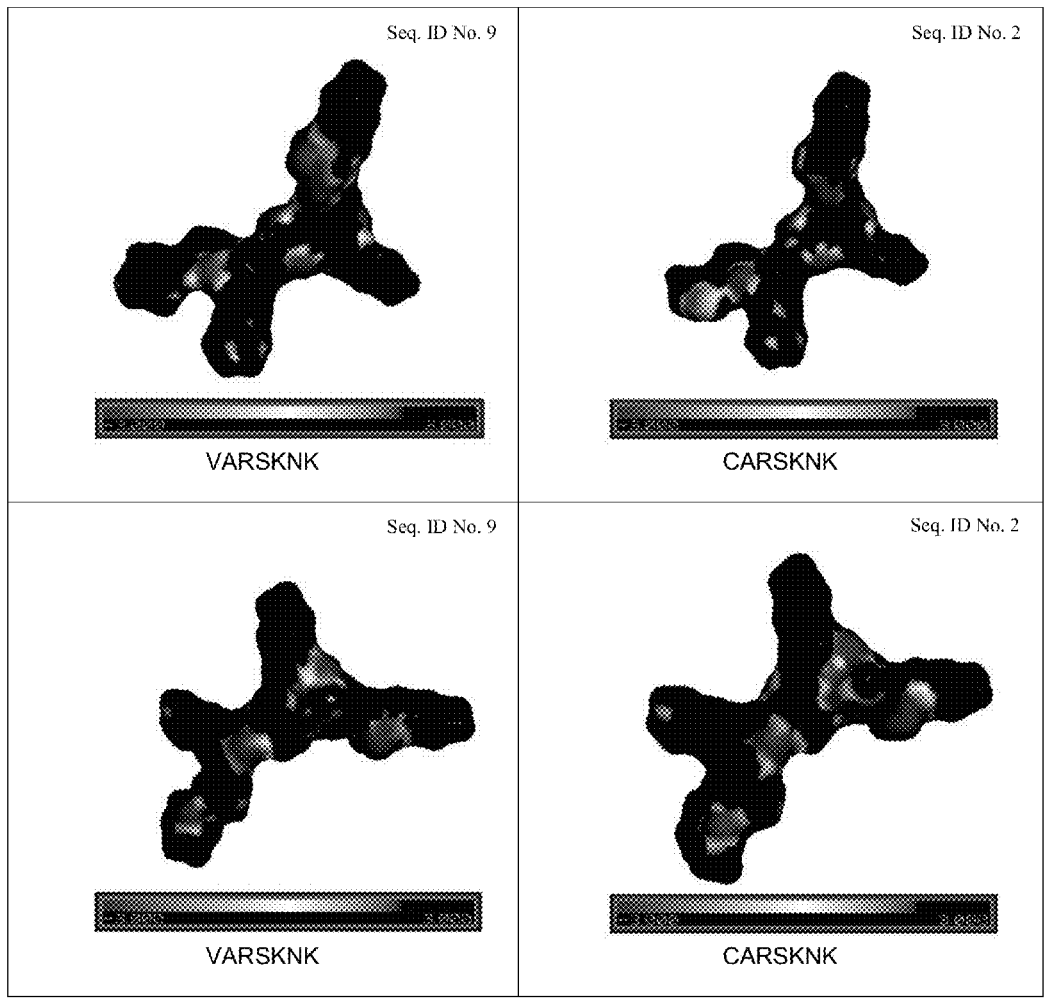

FIG. 35 shows a conformational comparison between the electrostatic potential surface structure of CARK (right images) and a substitutional variant VARSKNK (SEQ ID NO: 9) (left images) in which Valine (V) has been substituted for the N terminus cysteine (C).

Figure 36:
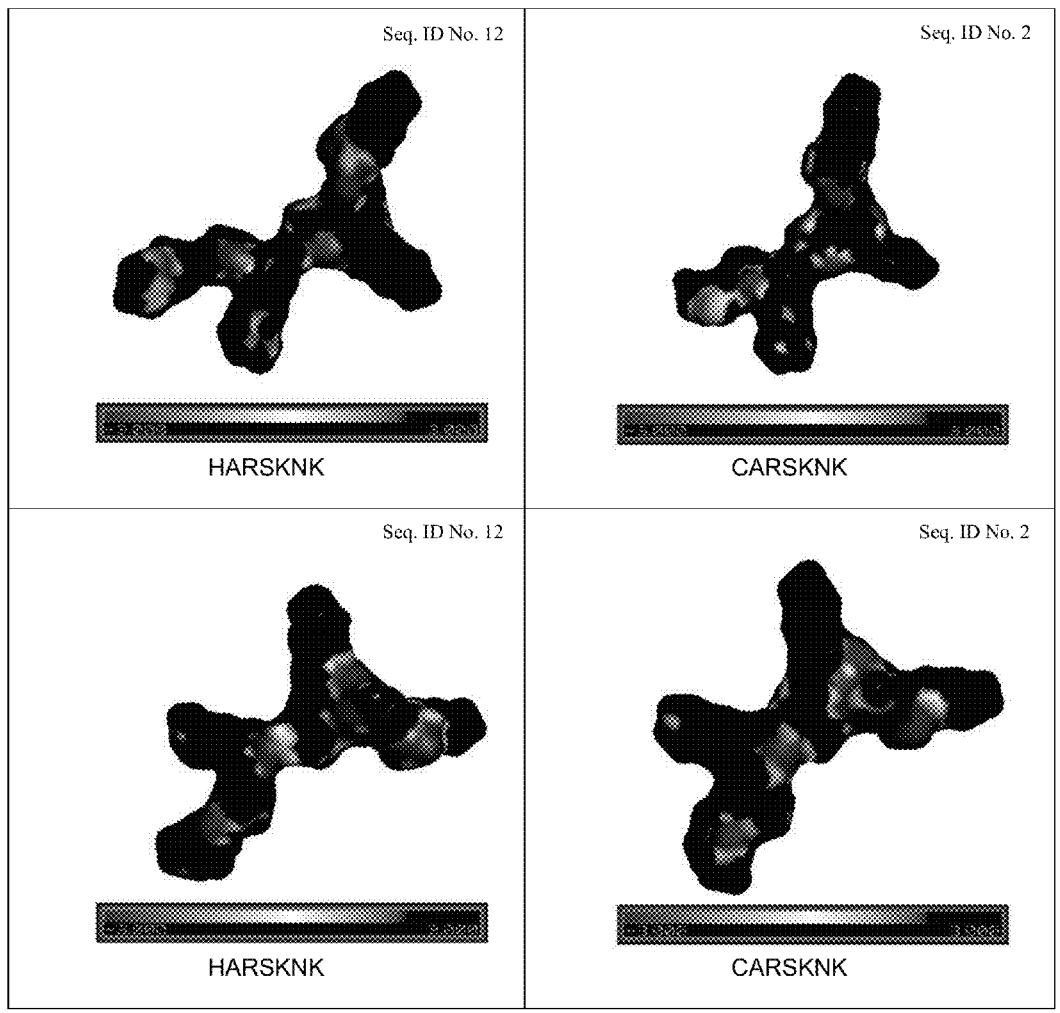

FIG. 36 shows a conformational comparison between the electrostatic potential surface structure of CARK (right images) and a substitutional variant HARSKNK (SEQ ID NO: 12) (left images) in which alanine (A) has been substituted for the N terminus cysteine (C).

Figure 37:
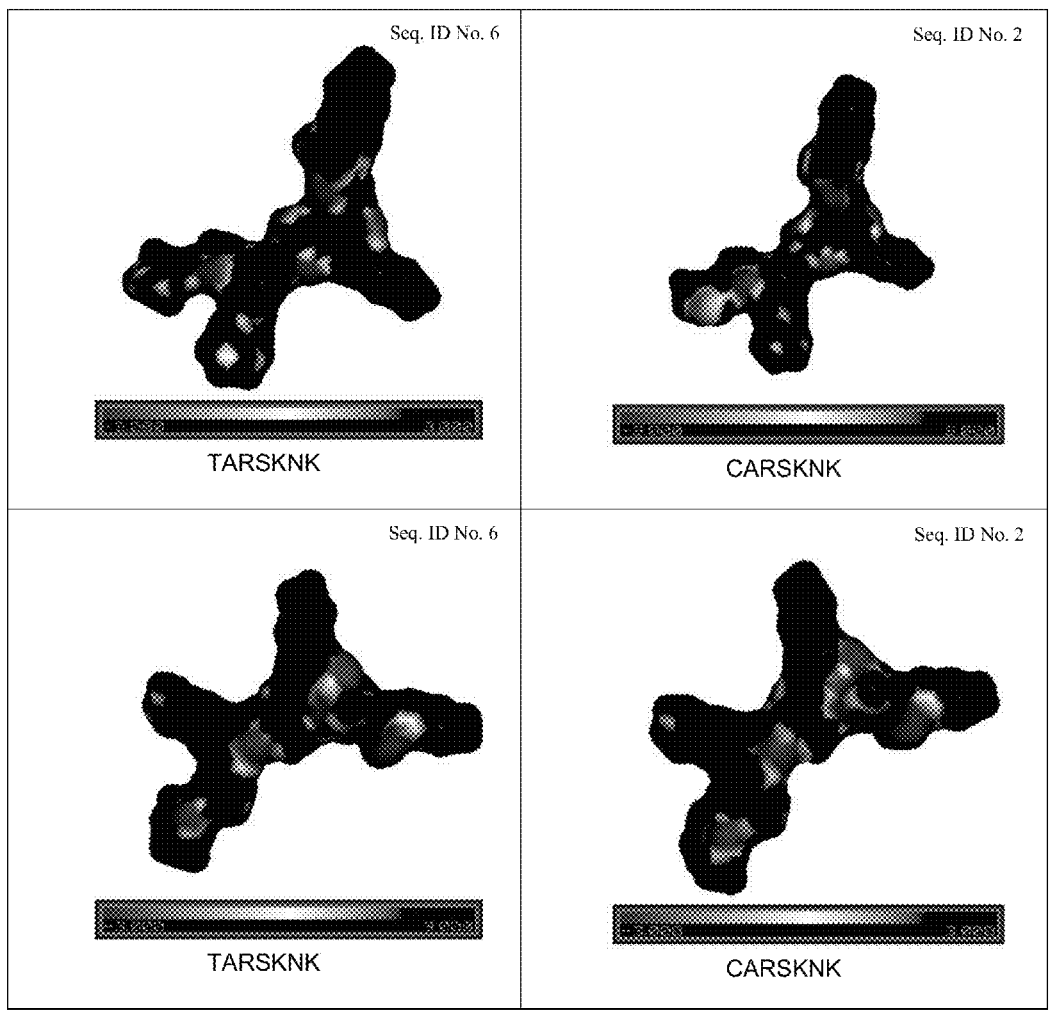

FIG. 37 shows a conformational comparison between the electrostatic potential surface structure of CARK (right images) and a substitutional variant TARSKNK (SEQ ID NO: 6) (left images) in which Threonine (T) has been substituted for the N terminus cysteine (C).

Figure 38:
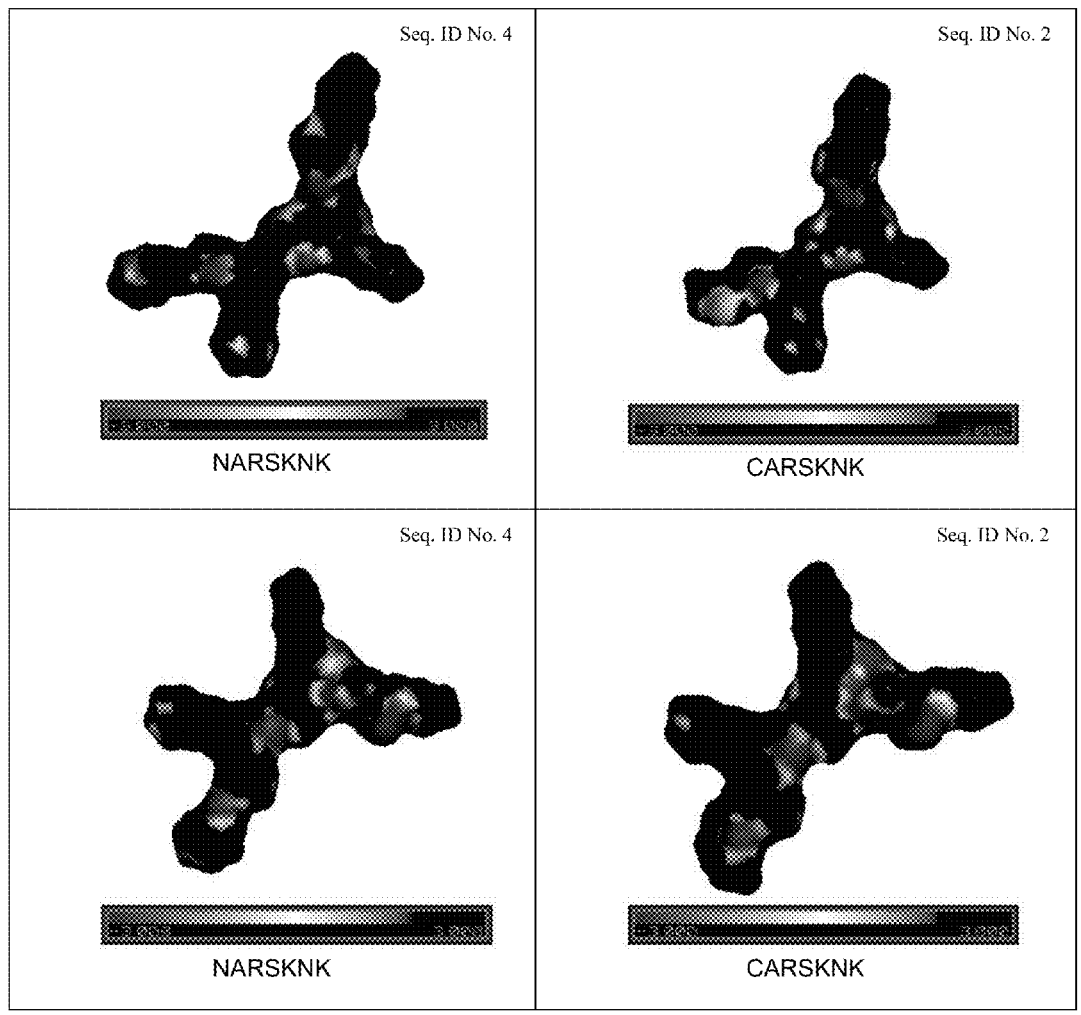

FIG. 38 shows a conformational comparison between the electrostatic potential surface structure of CARK (right images) and a substitutional variant NARSKNK (SEQ ID NO: 4) (left images) in which asparagine (N) has been substituted for the N terminus cysteine (C).

Figure 39:
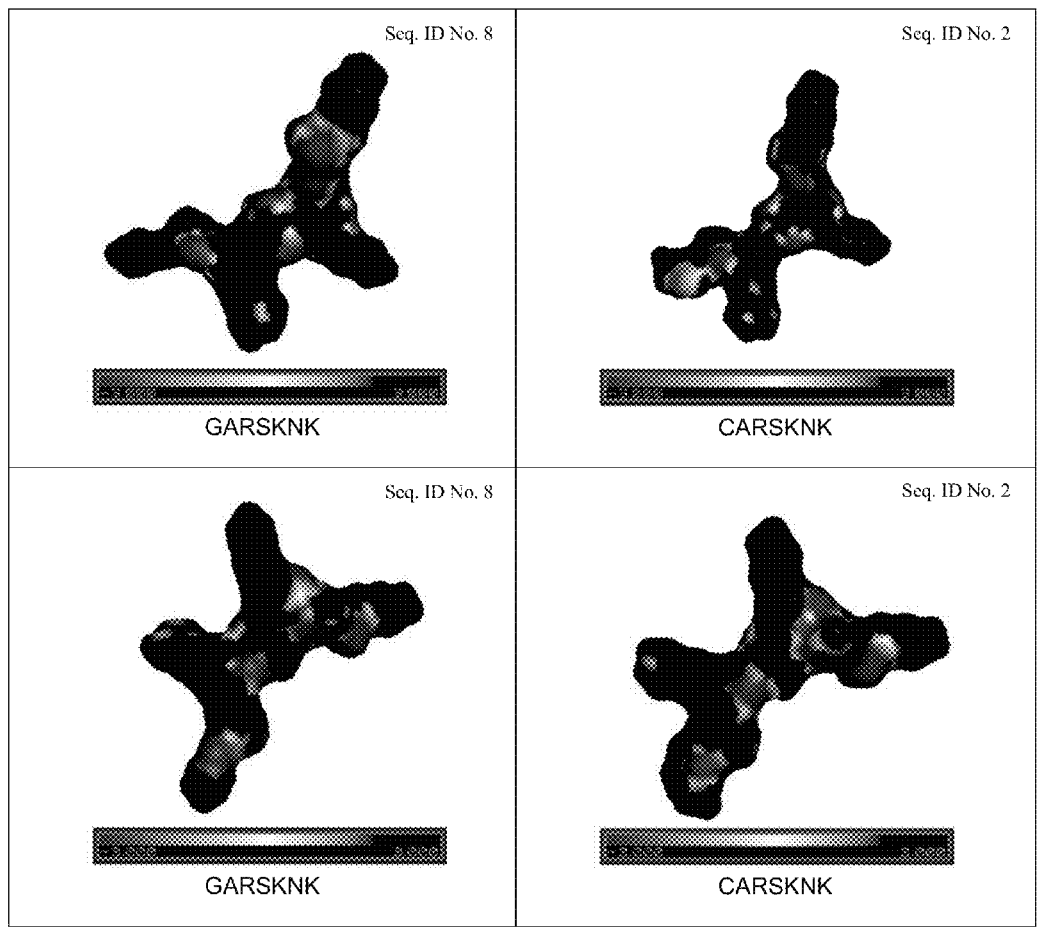

FIG. 39 shows a conformational comparison between the electrostatic potential surface structure of CARK (right images) and a substitutional variant GARSKNK (SEQ ID NO: 8) (left images) in which glutamic acid (G) has been substituted for the N terminus cysteine (C).

Figure 40:
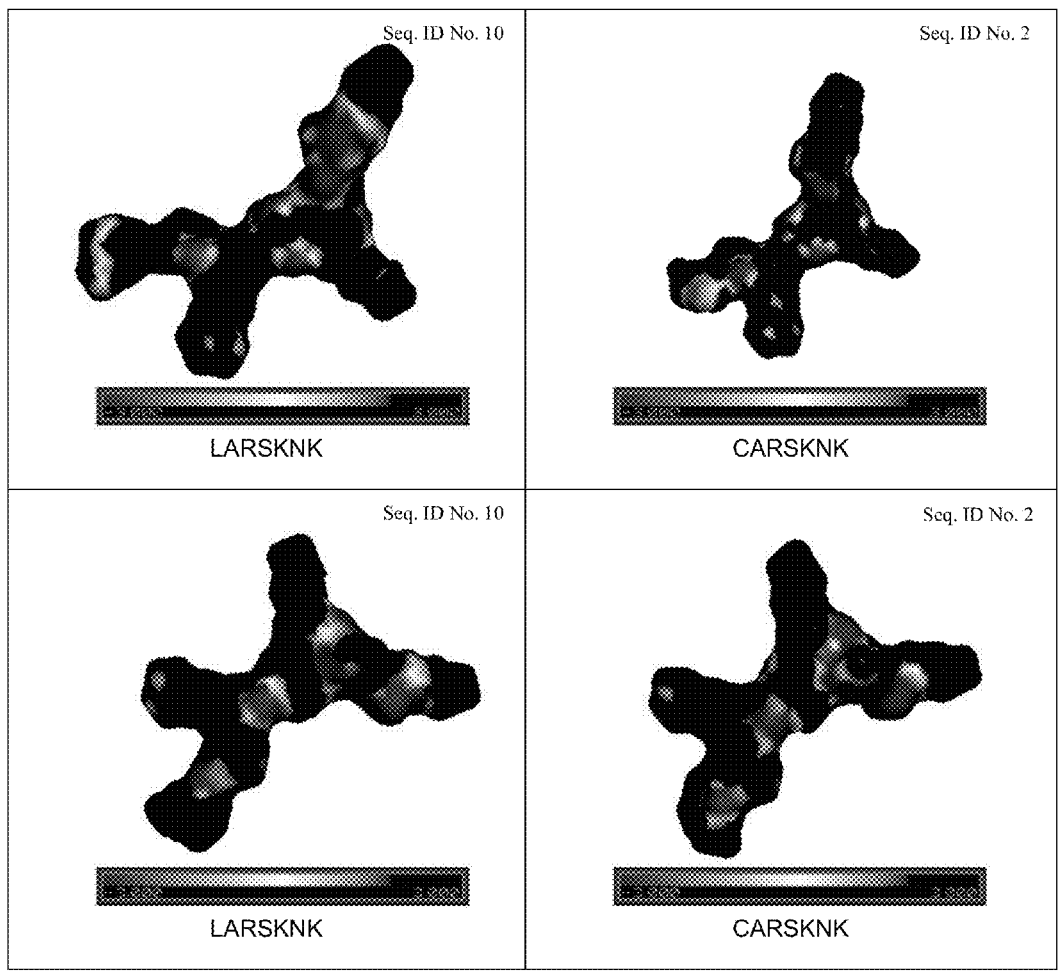

FIG. 40 shows a conformational comparison between the electrostatic potential surface structure of CARK (right images) and a substitutional variant LARSKNK (SEQ ID NO: 10) (left images) in which leucine (L) has been substituted for the N terminus cysteine (C).

Figure 41:
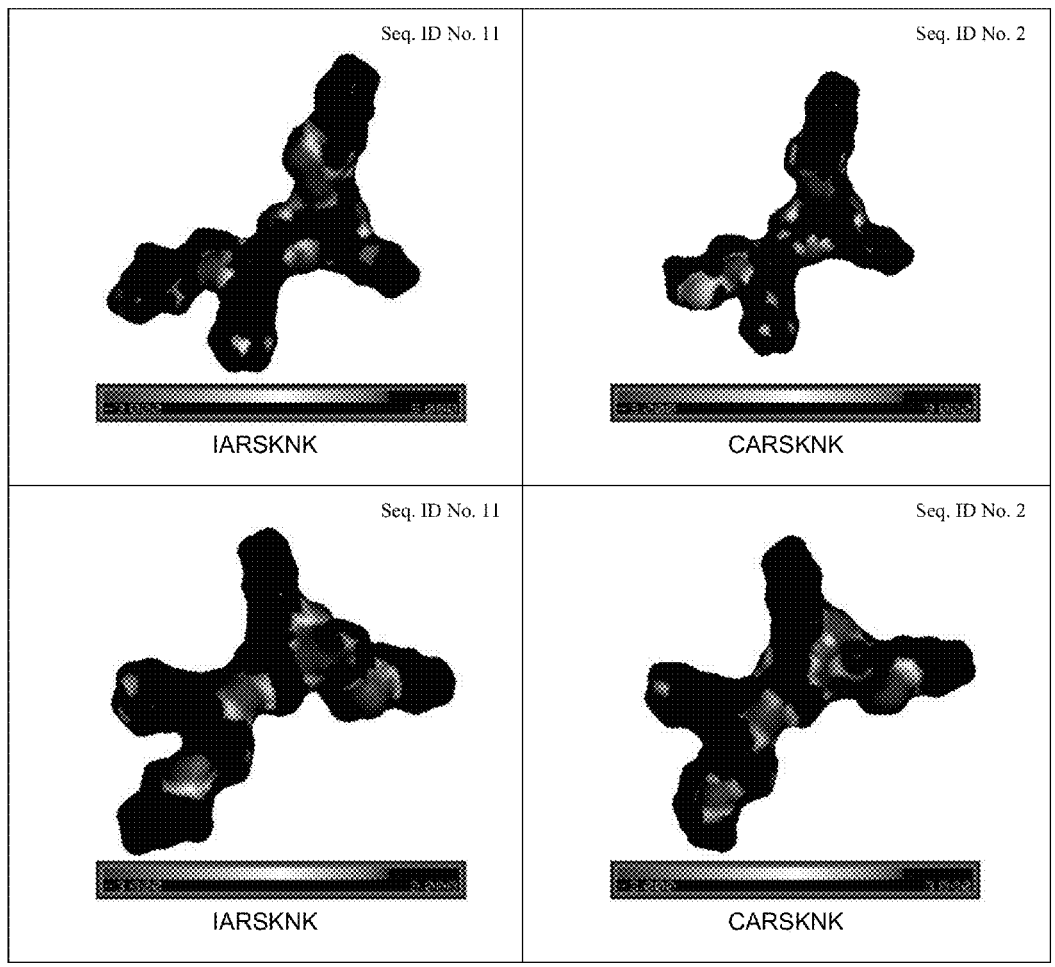

FIG. 41 shows a conformational comparison between the electrostatic potential surface structure of CARK (right images) and a substitutional variant IARSKNK (SEQ ID NO: 11) (left images) in which isoleucine (I) has been substituted for the N terminus cysteine (C).

Figure 42:
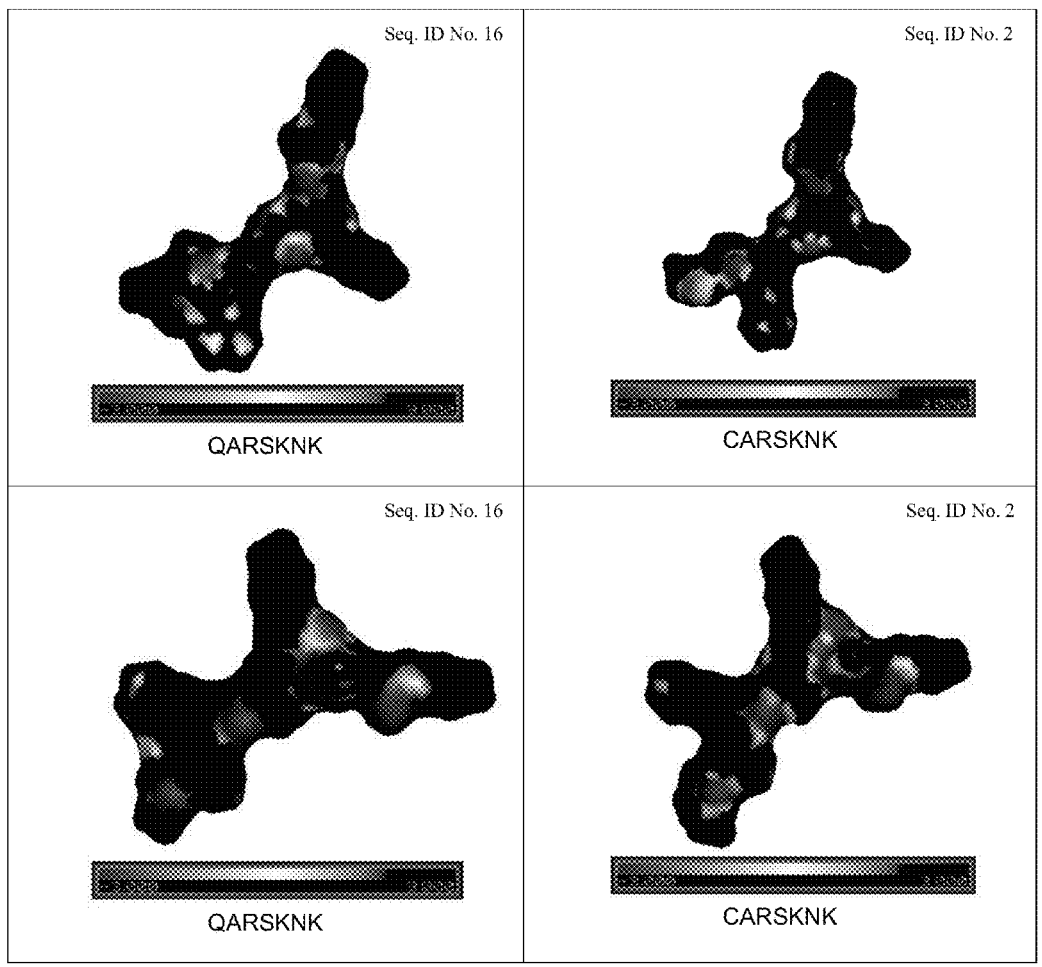

FIG. 42 shows a conformational comparison between the electrostatic potential surface structure of CARK (right images) and a substitutional variant QARSKNK (SEQ ID NO: 16) (left images) in which glutamiine (Q) has been substituted for the N terminus cysteine (C).

Figure 43:
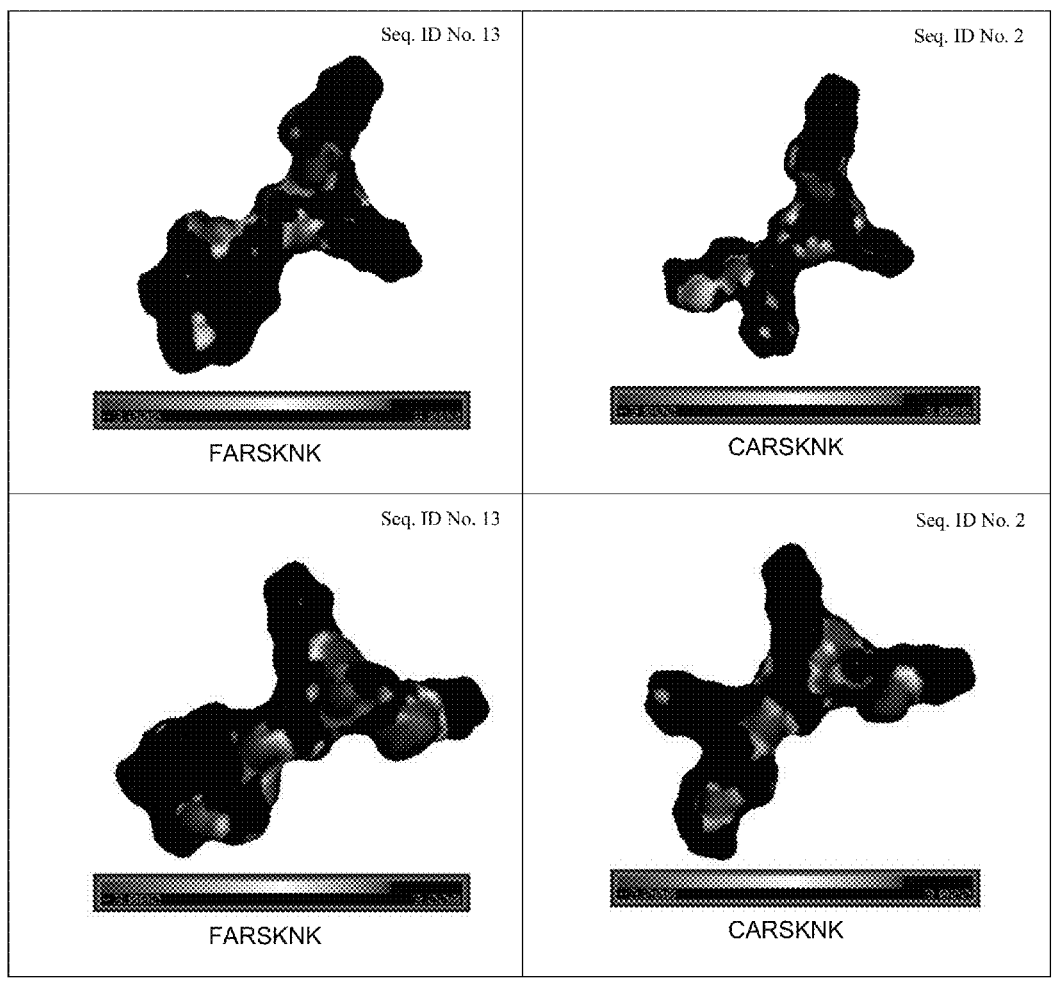

FIG. 43 shows a conformational comparison between the electrostatic potential surface structure of CARK (right images) and a substitutional variant FARSKNK (SEQ ID NO: 13) (left images) in which alanine (A) has been substituted for the N terminus cysteine (C).

Figure 44:
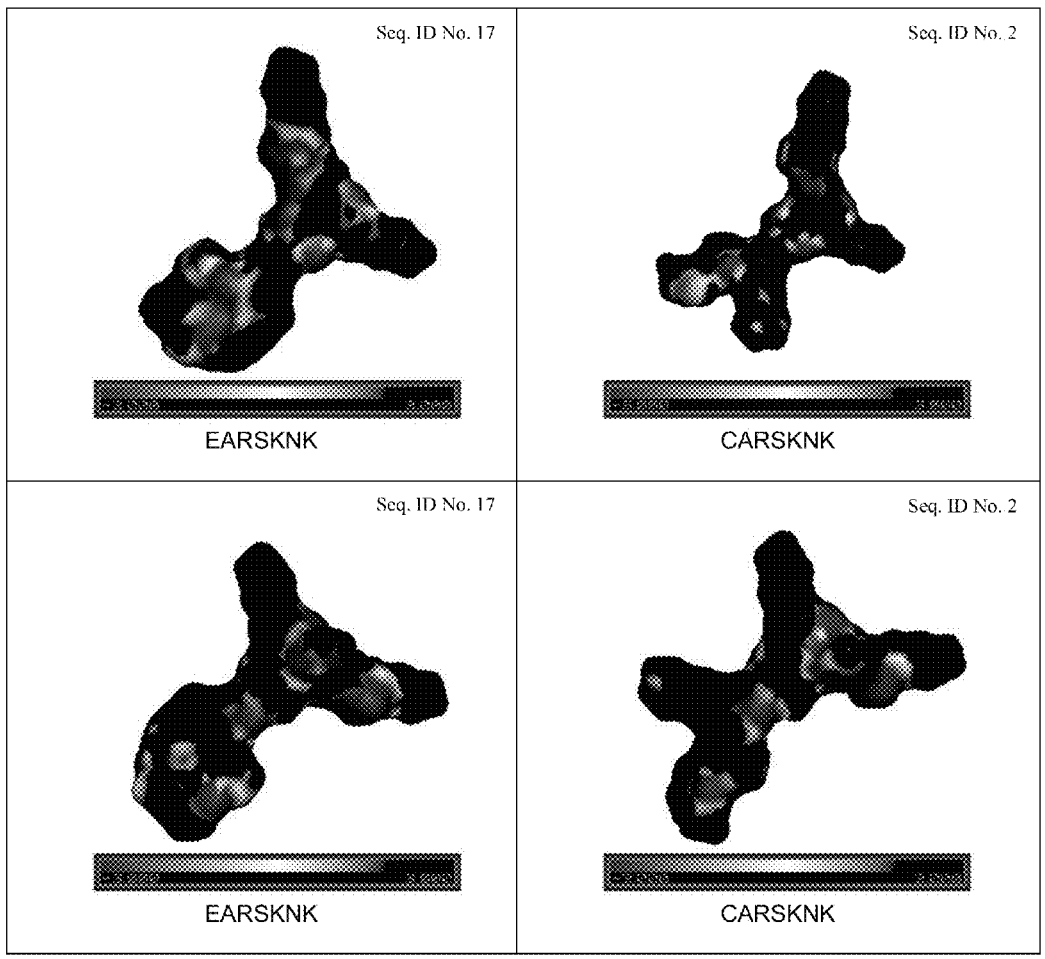

FIG. 44 shows a conformational comparison between the electrostatic potential surface structure of CARK (right images) and a substitutional variant EARSKNK (SEQ ID NO: 17) (left images) in which phenylalanine (F) has been substituted for the N terminus cysteine (C).

Figure 45:
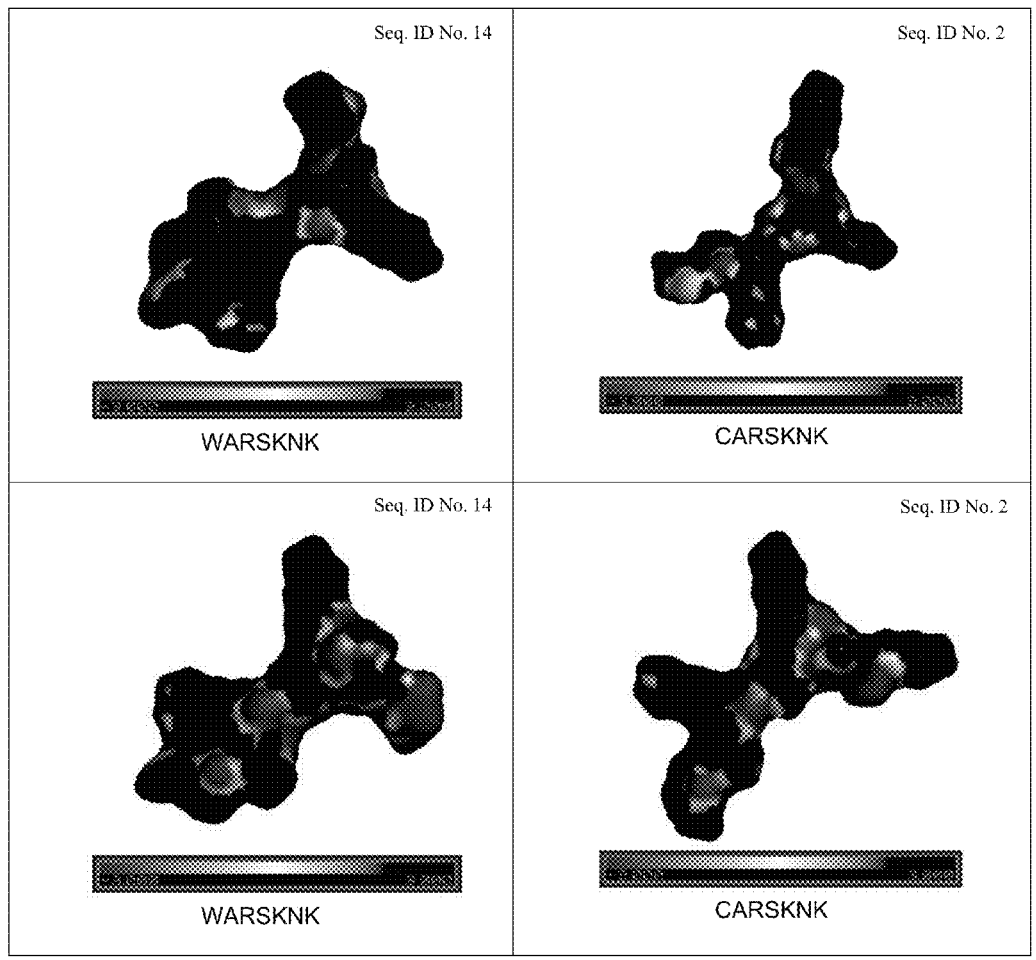

FIG. 45 shows a conformational comparison between the electrostatic potential surface structure of CARK (right images) and a substitutional variant WARSKNK (SEQ ID NO: 14) (left images) in which tryptophan (W) has been substituted for the N terminus cysteine (C).

Figure 46:
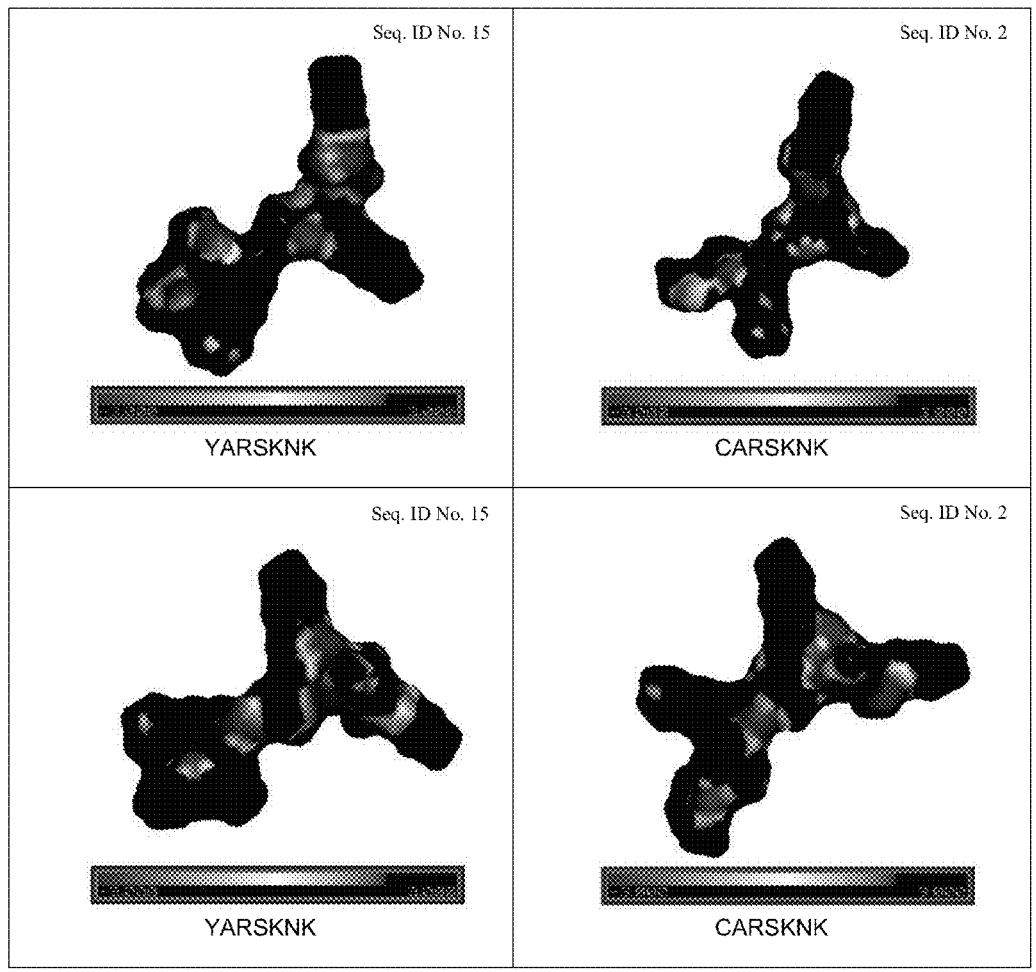

FIG. 46 shows a conformational comparison between the electrostatic potential surface structure of CARK (right images) and a substitutional variant YARSKNK (SEQ ID NO: 15) (left images) in which tyrosine (Y) has been substituted for the N terminus cysteine (C).

Figure 47:
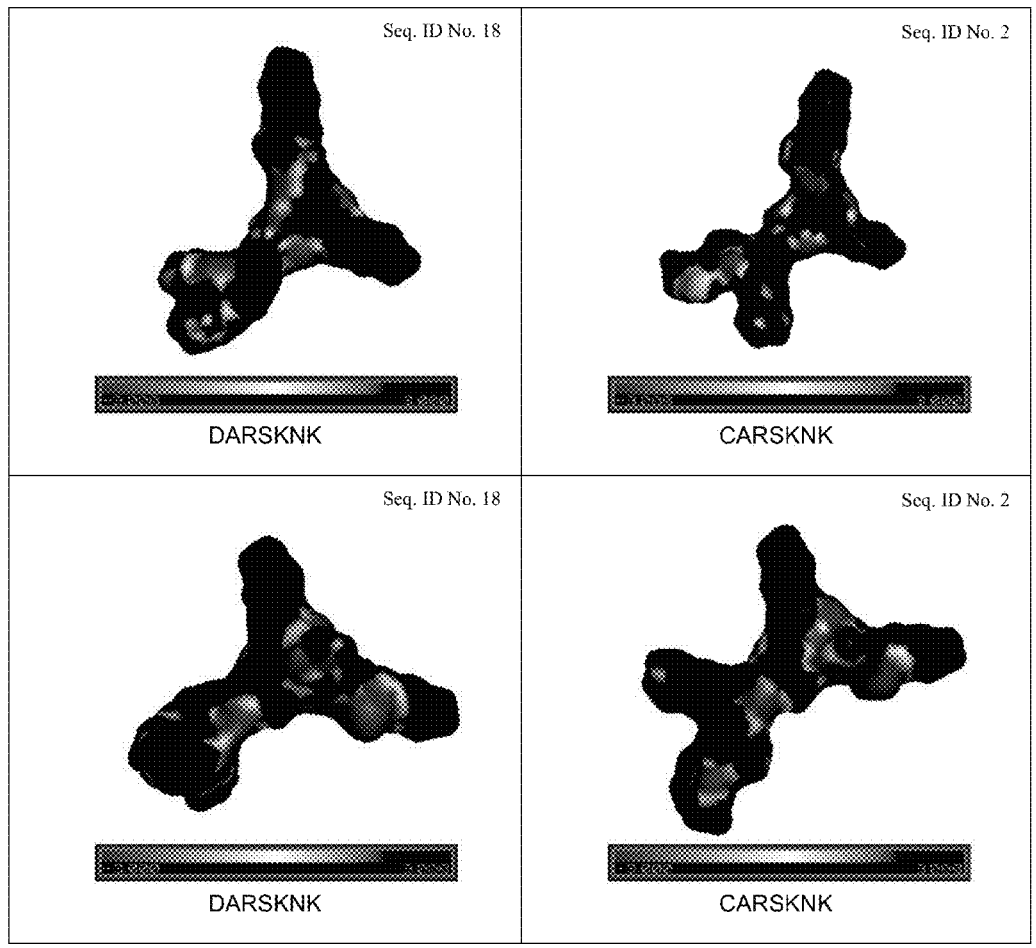

FIG. 47 shows a conformational comparison between the electrostatic potential surface structure of CARK (right images) and a substitutional variant DARSKNK (SEQ ID NO: 18) (left images) in which aspartic acid (D) has been substituted for the N terminus cysteine (C).

Figure 48:
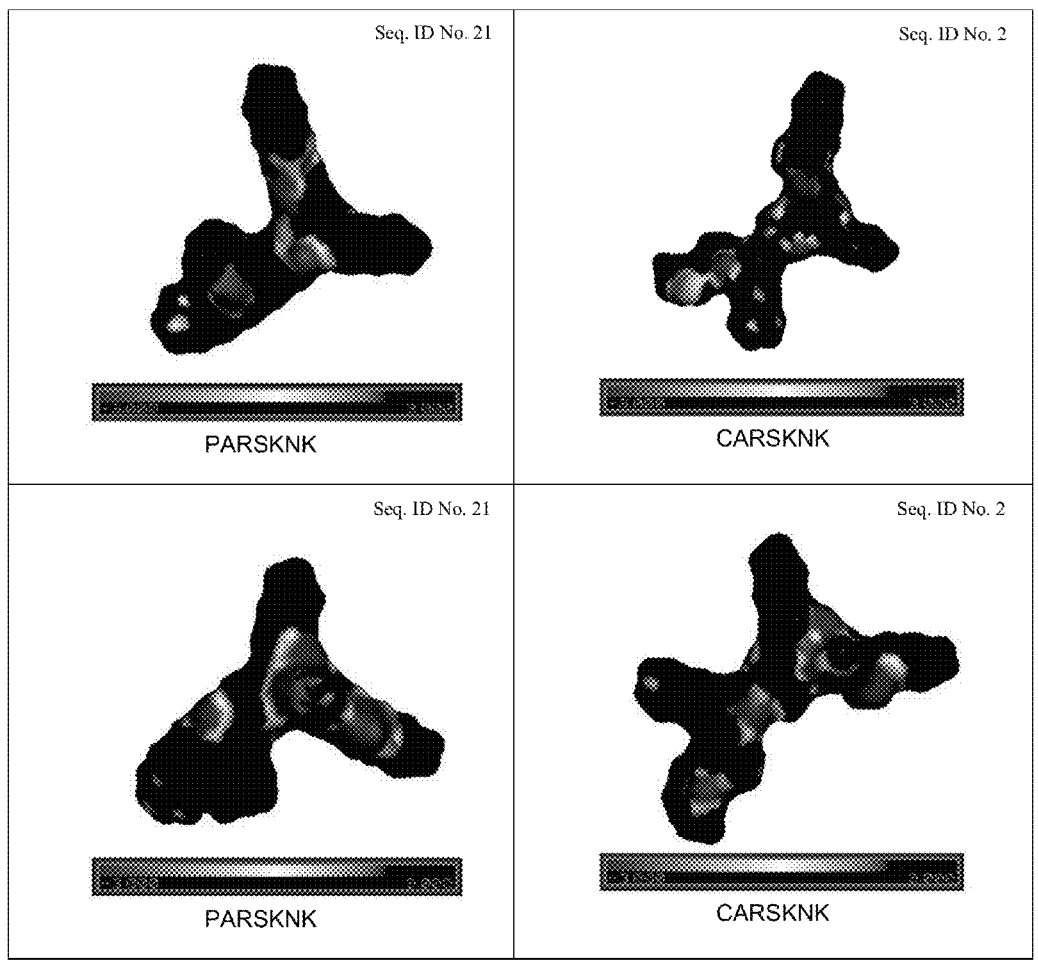

FIG. 48 shows a conformational comparison between the electrostatic potential surface structure of CARK (right images) and a substitutional variant PARSKNK (SEQ ID NO: 21) (left images) in which proline (P) has been substituted for the N terminus cysteine (C).

Figure 49:
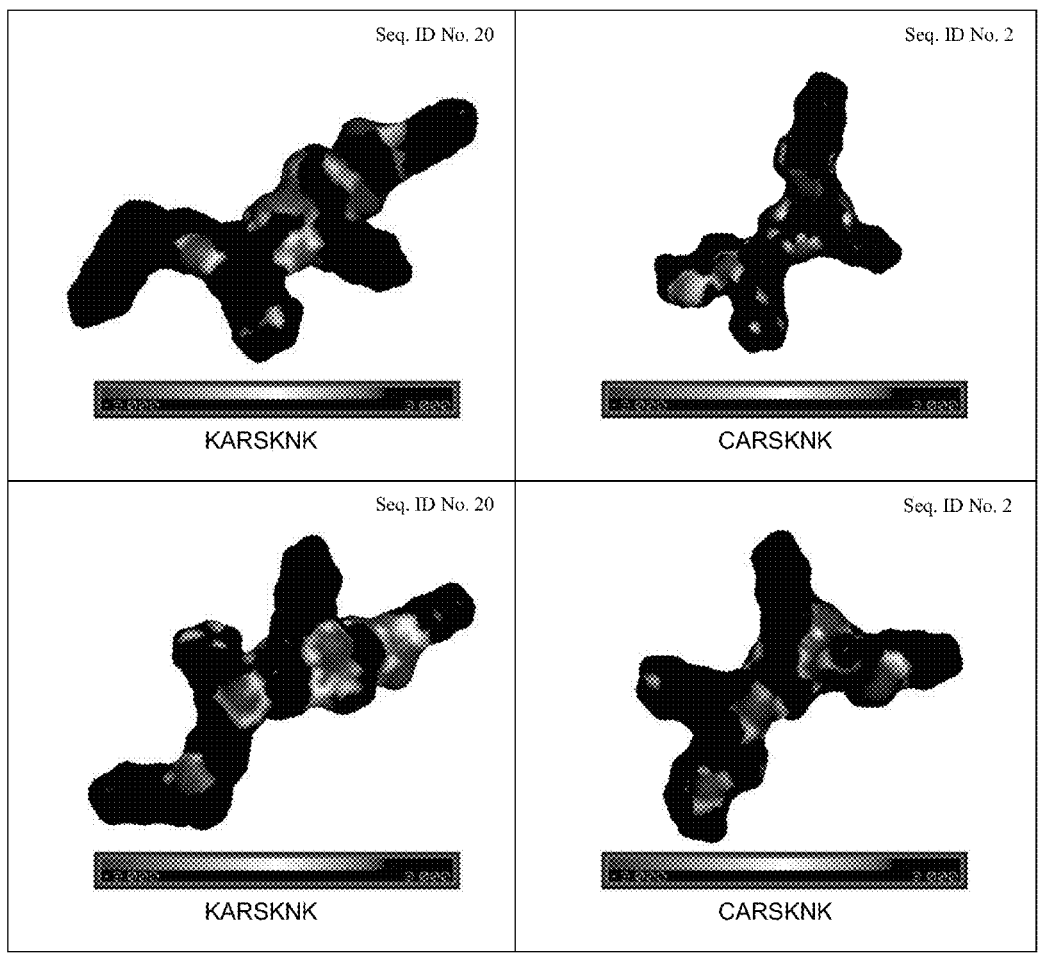

FIG. 49 shows a conformational comparison between the electrostatic potential surface structure of CARK (right images) and a substitutional variant KARSKNK (SEQ ID NO: 20) (left images) in which lysine (K) has been substituted for the N terminus cysteine (C).

Figure 50:
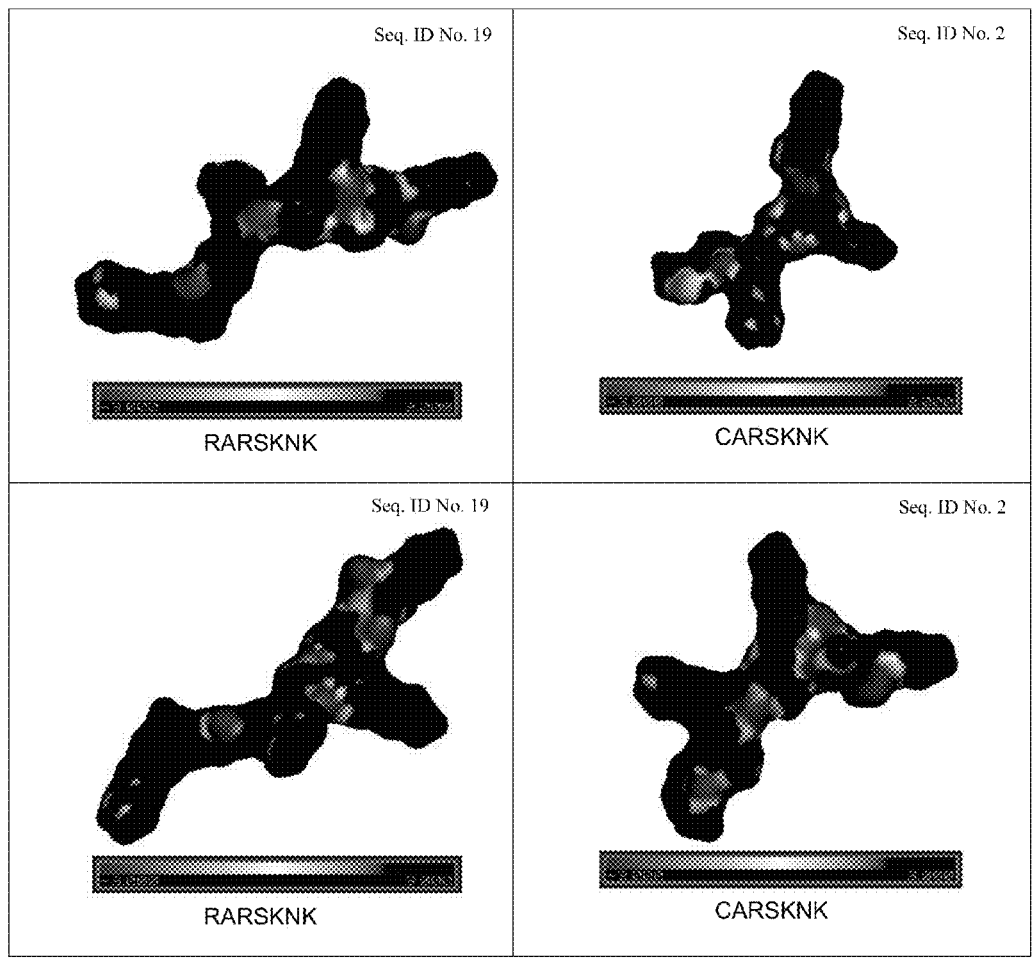

FIG. 50 shows a conformational comparison between the electrostatic potential surface structure of CARK (right images) and a substitutional valiant RARSKNK (SEQ ID NO: 19) (left images) in which arginine (R) has been substituted for the N terminus cysteine (C).

Figure 51:
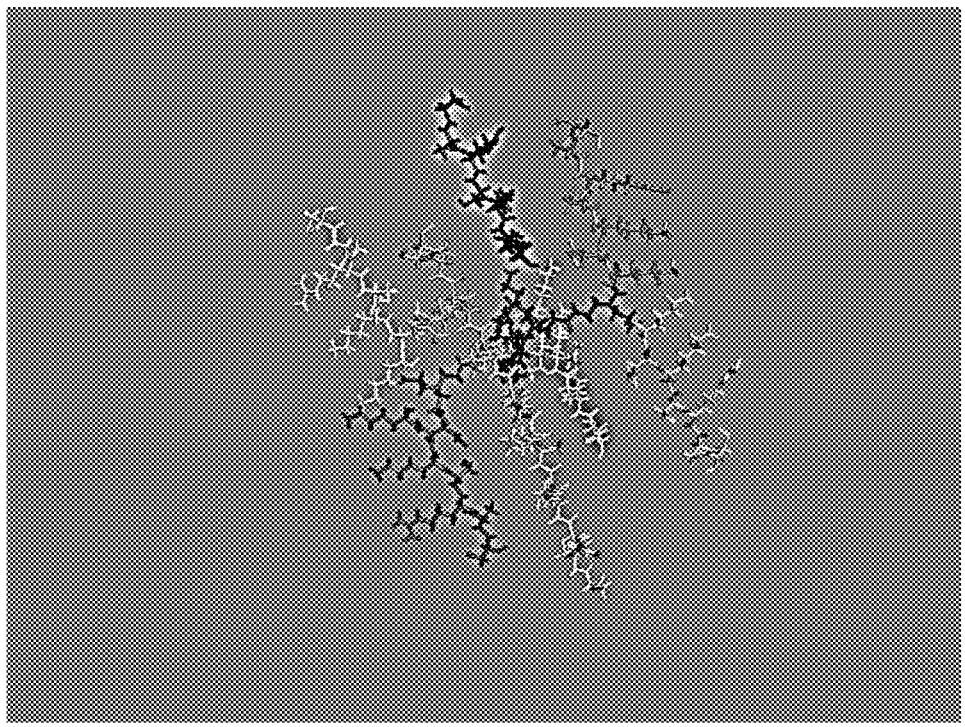

FIG. 51 shows the molecular structure in sticks of a CARK 8-mer dendrimer composed of 8 copies of CARK connected to a polyamidoamine core.

Figure 52:
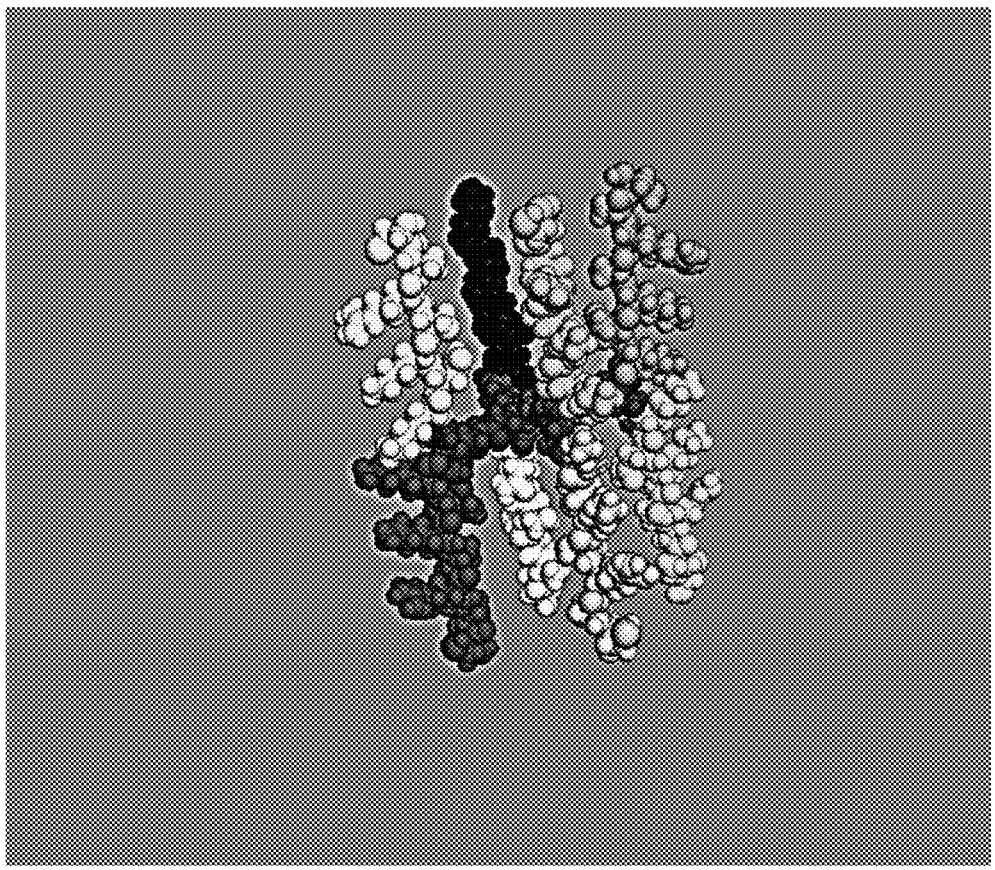

FIG. 52 shows the molecular structure in space filling balls of a CARK 8-mer dendrimer composed of 8 copies of CARK connected to a polyamidoamine core.

SUMMARY OF THE INVENTION

In one embodiment, the present invention provides for a composition comprising: (a) a targeting peptide comprising at least one amino acid sequence having substantial identity to a sequence selected from the group consisting of SEQ ID NO:1 and SEQ ID NO:2, and (b) at least one bioactive agent which conveys a measureable therapeutic benefit to a disease. Preferably, the disease is selected from the group consisting of pulmonary hypertension, interstitial lung disease, acute lung injury (ALI), acute respiratory distress syndrome (ARDS), sepsis, septic shock, sarcoidosis of the lung, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, non-alcoholic fatty liver disease, nonalcoholic steatohepatitis, sarcoidosis of the lymph nodes, or other organs, inflammatory bowel disease, crohn's disease, ulcerative colitis, primary biliary cirrhosis, pancreatitis, interstitial cystitis, chronic obstructive pulmonary disease, pneumoconiosis, autoimmune diseases, angiogenic diseases, wound healing, infections, trauma injuries and systemic connective tissue diseases including systemic lupus erythematosus, rheumatoid arthritis, scleroderma, polymyositis, and dermatomyositis.

Alternatively, the targeting peptide comprises the amino acid sequence of SEQ ID NO:1. In another embodiment, the targeting peptide comprises the amino acid sequence of SEQ ID NO:2. In yet another embodiment, the targeting peptide is animal, bacterial, viral or synthetic in origin. An alternative embodiment is disclosed, wherein the targeting peptide and the at least one bioactive agent are in bound together. Alternatively, the targeting peptide and the at least one bioactive agent are in an unbound configuration. In yet another embodiment, the at least one bioactive agent is specific for the disease to be treated. Alternatively, the at least one bioactive agent is non-specific for the disease to be treated.

In another embodiment, the present invention describes a method of preventing or treating a disease comprising the steps of: (a) providing a targeting peptide comprising at least one amino acid sequence having substantial identity to a sequence selected from the group consisting of SEQ ID NO:1 and SEQ ID NO:2; (b) providing at least one bioactive agent which conveys a measureable therapeutic benefit to the disease; (c) co-administering a composition comprising (a) and (b) to an animal in need thereof; and (d) measuring the therapeutic benefit to the animal. Alternatively, the disease to be treated is pulmonary or fibrotic. In yet another alternative embodiment, the disease to be treated is cancer. In yet another embodiment, the disease to be treated is an autoimmune disease. In yet a further embodiment, the disease to be treated is an inflammatory disease. Alternatively, the targeting peptide of the disclosed method comprises on the amino acid sequence of SEQ ID NO:1. In another embodiment, the targeting peptide of the disclosed method comprises on the amino acid sequence of SEQ ID NO:2. In yet another embodiment, the targeting peptide is animal, bacterial, viral or synthetic in origin. An alternative embodiment is disclosed, wherein the targeting peptide and the at least one bioactive agent are in bound together. Alternatively, the targeting peptide and the at least one bioactive agent are in an unbound configuration. In yet another embodiment, the at least one bioactive agent is specific for the disease to be treated. Alternatively, the at least one bioactive agent is non-specific for the disease to be treated.

In still another embodiment, the present invention describes a method of detecting an enhanced targeting effect of cell penetrating peptides in an animal comprising the steps of: (a) analyzing a sample from the animal for an altered level of at least one gene expression when compared to a control, wherein the at least on gene expressed encodes for a proteoglycan enzyme; (b) correlating the altered level of at least one gene expression in the sample with the enhanced targeting effect of cell penetrating peptides; and (c) treating the animal with a therapeutic composition comprising at least one cell penetrating peptide and at least one bioactive agent. In an alternative embodiment, the at least one gene expressed encodes for an enzyme involved in heparan sulfate biosynthesis. Another embodiment provides for the altered level of at least one gene expression being an elevated level of the at least one gene expression. Alternatively, the at least one gene having the altered level of expression is selected from the group consisting of heparan sulfate 2-O-sulfotransferase 1, exostosin 1, glycosyltransferase 8 domain containing 2, heparan sulfate N-deacetylase/N-sulfotransferase and O-linked N-acetylglucosamine transferase. Alternatively, the enhanced targeting effect is targeted to heparan sulfate. In yet another embodiment, the therapeutic binds to heparan sulfate. In still another embodiment, the at least one cell penetrating peptide is selected from the group consisting of SEQ ID NO:1 and SEQ ID NO:2.

In yet another embodiment, the present invention provides for a method of treatment, comprising: (a) providing a targeting peptide comprising at least one amino acid sequence having substantial identity to a sequence selected from the group consisting of SEQ ID NO: 1 and SEQ ID NO:2; (b) providing at least one bioactive agent which conveys a measureable therapeutic benefit to the disease; (c) co-administering a composition comprising (a) and (b) to an animal in need thereof, wherein the disease is associated with at least one alteration in heparan sulfate gene expression levels and the composition comprising (a) and (b) is targeted to at least one heparan sulfate receptor.

DETAILED DESCRIPTION OF THE INVENTION

Definitions

The term "bioactive agent" refers to a substance which is used in connection with an application that is therapeutic or diagnostic in nature, such as in methods for diagnosing the presence or absence of a disease in a patient and/or in methods for treating a disease in a patient. As to compatible bioactive agents, those skilled in the art will appreciate that any therapeutic or diagnostic agent may be incorporated in the stabilized dispersions of the present invention. For example, the bioactive agent may be selected from the group consisting of antiallergics, bronchodilators, vasodilators, antihypertensive agents, bronchoconstrictors, pulmonary lung surfactants, analgesics, antibiotics, leukotriene inhibitors or antagonists, anticholinergics, mast cell inhibitors, antihistamines, anti-inflammatories, anti-neoplastics, anesthetics, anti-tuberculars, imaging agents, cardiovascular agents, enzymes, steroids, genetic material, viral vectors, antisense agents, small molecule drugs, proteins, peptides and combinations thereof. Particularly preferred bioactive agents comprise compounds which are to be administered systemically (i.e. to the systemic circulation of a patient) such as small molecule drugs, imaging agents, peptides, proteins or polynucleotides. As will be disclosed in more detail below, the bioactive agent may be incorporated, blended in, coated on or otherwise associated with the targeting peptide disclosed herein. Particularly preferred bioactive agents for use in accordance with the invention include anti-allergies, peptides and proteins, bronchodilators, anti-inflammatory agents and anti-cancer compounds for use in the treatment of disorders involving diseased tissue reflecting altered heparan sulfate variants specific to said disease. Yet another associated advantage of the present invention is the effective delivery of bioactive agents administered or combined with a targeting peptide.

The phrase "substantially identical" means that a relevant sequence is at least 70%, 75%, 80%, 85%, 90%, 92%, 95% 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. See Zubay, Biochemistry, Addison-Wesley Pub. Co., (1983). It is a well-established principle of protein and peptide chemistry that certain amino acids substitutions, entitled "conservative" amino acid substitutions, can frequently be made in a protein or a peptide without altering either the conformation or the function of the protein or peptide. Such changes include substituting any of alanine (A), isoleucine (I), valine (V), and leucine (L) for any other of these amino acids; aspartic acid (D) for glutamic acid (E) and vice versa; glutamine (Q) for asparagine (N) and vice versa; serine (S) for threonine (T) and vice versa; and arginine (R) for lysine (K) and vice versa.

In addition to the known functional variants, there are derivatives of the peptides disclosed herein which can also function in the disclosed methods and compositions. Protein and peptide variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about from 2 to 6 residues are deleted at any one site within the protein or peptide molecule. These variants can be prepared by site-specific mutagenesis of nucleotides in the DNA encoding the protein or peptide, thereby producing DNA encoding the variant, and thereafter expressing the DNA in recombinant cell culture, or via solid state peptide synthesis.

Techniques for making substitution mutations at predetermined sites in DNA having a known sequence are well known. Amino acid substitutions are typically of single residues, but can occur at a number of different locations at once; insertions usually will be on the order of about from 1 to 10 amino acid residues; and deletions will range about from 1 to 10 residues. Deletions or insertions preferably are made in adjacent pairs, i.e. a deletion of 2 residues or insertion of 2 residues. Substitutions, deletions, insertions or any combination thereof can be combined to arrive at a final construct. The mutations generally should not place the sequence out of reading frame (unless a truncated peptide is intended) and preferably will not create complementary regions that could produce secondary mRNA structure.

Substitutional variants are those in which at least one residue has been removed and a different residue inserted in its place. Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or praline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. Similarly, the term "conformational homology" may be used herein to define a sequence which maintains a similar arrangement of amino acids from a conformational perspective to SEQ ID NO:1 or SEQ ID NO:2.

As used herein, the term "peptide" is used broadly to mean peptides, proteins, fragments of proteins and the like. The peptide may be animal, bacterial, viral or synthetic in origin. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an .alpha.-methylated amino acid; .alpha.,.alpha.-dialkylglycine or .alpha.-aminocycloalkane carboxylic acid; an N.sup.alpha.-C.sup.alpha. cyclized amino acid; an N:sup.alpha.-methylated amino acid; a .beta.- or .gamma.-amino cycloalkane carboxylic acid; an .alpha.,.beta.-unsaturated amino acid; a .beta.,.beta.-dimethyl or .beta.-methyl amino acid; a .beta.-substituted-2,3-methano amino acid; an N-C.sup.epsilon. or C.sup.alpha.-C.sup.delta. cyclized amino acid; a substituted proline or another amino acid mimetic. A peptidomimetic which mimics peptide secondary structure can contain, for example, a non-peptidic .beta.-turn mimic; .gamma.-turn mimic; mimic of .beta.-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

As used herein, the term "dendrimer" shall mean repeatedly branched and roughly spherical molecules. A dendrimer is typically symmetric around a core and usually adopts a spherical three-dimensional morphology. Dendrimers generally contain three major portions: a core, an inner shell and an outer shell. Dendrimers can be synthesized to have different and varying functionality in each of the major portions in order to control such variables as solubility, thermal stability and attachment of compounds suitable for particular applications.

CARSKNKDC (SEQ ID NO: 1) (CAR) peptide has been previously been shown to target wound healing (Järvinen and Ruoslahti, 2007). CAR peptide has also been linked to decorin for targeted anti-TGF-β scar minimization in skin wounds (Jarvinen and Ruoslahti, 2010).

Here we describe the novel homing of CAR peptides to hypertensive pulmonary vasculature, acutely injured pulmonary tissue, and fibrotic pulmonary tissue. Additionally, we disclose a novel means of achieving targeted therapy with CAR via simultaneous administration of CAR peptide along with another therapeutic.

These findings provide the means to diagnose and deliver targeted therapies for pulmonary diseases such as pulmonary hypertension, interstitial lung disease, acute lung injury (ALI), acute respiratory distress syndrome (ARDS), sepsis, septic shock, sarcoidosis of the lung, pulmonary manifestations of connective tissue diseases, including systemic lupus erythematosus, rheumatoid arthritis, scleroderma, and polymyositis, dermatomyositis, bronchiectasis, asbestosis, berylliosis, silicosis, Histiocytosis X, pneumotitis, smoker's lung, bronchiolitis obliterans, the prevention of lung scarring due to tuberculosis and pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, keloid, arthrofibrosis, adhesive capsulitis, radiation fibrosis, fibrocystic breast condition, liver cirrhosis, hepatitis, liver fibrosis, nonalcoholic fatty liver disease, non-alcoholic steatohepatitis, sarcoidosis of the lymph nodes, or other organs; inflammatory bowel disease, crohn's disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, angiogenic diseases, wound healing, infections, trauma injuries and systemic connective tissue diseases including systemic lupus erythematosus, rheumatoid arthritis, scleroderma, polyrnyositis, and dermatomyositis.

These diseases can be treated by simultaneously administering CAR peptide with the bioactive agent to be targeted to the site of disease. We define simultaneous administration, or co-administration, as administration of CAR followed by administration of the therapeutic to be targeted within 1 hour of CAR administration. For example, if the disease is pulmonary hypertension and the desired goal is targeted pulmonary arterial vasodilation, an effective dose of CAR peptide can be co-administered with a minimal dose of systemic vasodilator to achieve targeted pulmonary vasodilation and a significant decrease in pulmonary pressure with minimal systemic hypotension.

Similarly, CAR peptide can be co-administered with other medications to increase therapeutic bioavailability, boost therapeutic efficacy, and minimize side effects. CAR may be administered in a linear or cyclical form, or in any conformation deemed physiologically appropriate as a means of conveying treatment.

In addition to targeted vasodilation, we can also deliver targeted anti-coagulation. For example, in a disease like acute lung injury, which is often marked by pulmonary intra-alveolar coagulation, targeted anti-coagulation can be delivered to the affected pulmonary area by co-administering an effective dose of CAR with an anti-coagulant such as tissue factor pathway inhibitor (TFPI) or site-inactivated factor VIIa (Welty-Wolf et al., 2001) in a minimal dose to achieve targeted pulmonary anticoagulation with minimal changes in clotting ability over the areas of the body not undergoing thrombosis. Selective pulmonary anti-coagulation can also be utilized to treat other pulmonary diseases marked by pulmonary thrombosis such as pulmonary hypertension, lung transplant rejection and others.

In a disease like chronic obstructive pulmonary disease, which is often marked by shortness of breath, CAR peptide can be co-administered to boost the effective concentration and potency of drugs to relax airway smooth muscles such as long lasting β-2 agonists such as salmeterol or formoterol (Richter, et al., 2002).

Many pulmonary diseases are often marked by a decrease in glutathione (GSH), a powerful antioxidant (Morris and Bernard, 1994). CAR peptide can be co-administered with N-Acetylcysteine (NAC), a glutathione precursor, in diseases like pulmonary fibrosis, PAH, ALI, and other pulmonary disorders to boost GSH production and scavenge reactive oxidants often found in pulmonary diseases. GSH may also serve to dampen the inflammatory immune response by binding to triggering receptor expressed on myeloid cells 1 (TREM1) and diminishing monocyte/macrophage- and neutrophil-mediated inflammatory responses. Co-administration of CAR with NAC can serve to lessen the severe inflammatory immune response that often characterizes severe pulmonary and fibrotic diseases like ALI, pulmonary hypertension, autoimmune diseases and many other conditions.

The levels of antioxidants such as Superoxide Dismutase (SOD) (Rosenfeld, et al., 1996), or synthetic superoxide dismutase mimetics like EUK-8 (Gonzalez et al., 1996) can be increased through co-administration of CAR.

Treatments for pulmonary diseases like pulmonary fibrosis, PAH and ALI can also be improved by co-administering CAR with TGF-β inhibitors like decorin. Decorin, which has been previously enhanced through direct conjugation with CAR (Janinen and Ruoslahti, 2010), can also be co-administered with CAR to achieve the benefits of targeting without direct conjugation between the CAR and decorin molecules.

In pulmonary hypertension, pulmonary fibrosis and other pulmonary diseases, the benefits of endothelin (ET-1) receptor antagonists (Kuklin et al., 2004), prostacyclin derivatives (Olschewski et al., 1999), phosphodiesterase type 5 inhibitors (Kanthapillai et al., 2004) and ontological agents such as imatinib (Ghofrani et al., 2005) (Aono et al., 2005) can be increased for patients through the co-administration of CAR.

Other pulmonary and fibrotic disease treatments such as Ketoconazole which inhibits thromboxane and leukotriene synthesis (Sinuff et al., 1999) can be improved in its efficacy while minimizing side effects through co-administration with CAR.

Newer therapeutic approaches such as small interfering RNA (siRNA), and microRNA (miRNA) therapies (Wurdinger and Costa, 2007) can also be improved and side effects minimized through the selective targeting of diseased tissue through the co-administration of CAR.

The present invention provides for establishing therapeutic targets by identifying altered gene expression levels at the heparan sulfate receptor, therefore indicating a diseased source. The diseased source may then be approached therapeutically with customized targeted therapies comprising a targeting peptide and bioactive agents disclosed in the present invention.

In addition to targeted therapies, CAR's homing to diseased pulmonary and fibrotic tissues can be utilized for the purposes of diagnosis through the conjugation or co-administration of CAR with imaging agents.

EXAMPLES

I. Monocrotaline Pulmonary Hypertension Model

Animal Model

Figure 1:
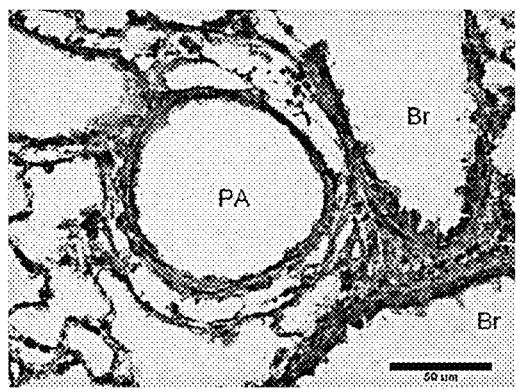
Figure 1:
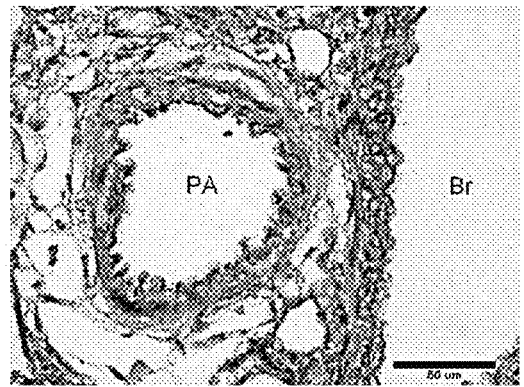

A rat model of monocrotaline (MCT)-induced pulmonary arterial hypertension was used for this study. Briefly, male Sprague-Dawley rats (150-200 g, Harlan Laboratories, IN) were administered with a single subcutaneous injection of monocrotaline at 60 mg/kg (Sigma-Aldrich, MO), while control rats administered 0.9% saline (FIG. 1). Rats were randomly selected and studied for peptide distribution studies on 1, 3, 7, 14 or 21 days after the treatment of monocrotaline.

Peptides

The following peptides were labeled with 5-carboxyfluorescein (5FAM) and used for the lung targeting studies: CAR, 5FAM-CARSKNKDC; VCAM1, CVHSPNKKCGGSK-5FAM; Control, 5FAM-CGGGGGGGC. All peptides were synthesized by Anaspec (Anaspec Inc., CA). Peptides were resolved in PBS at the concentrations of 0.5 mg/mL.

Peptide Targeting Study

MCT-treated or untreated rats were injected with peptide solution at a dose of 3.3 mg/kg body weight via the tail vein. At two hours after the injection, rats were perfused with PBS containing 1% bovine serum albumin under the deep anesthesia with isofluorane at a rate of 3.0% and euthanized. Tissues were fixed by systemic perfusion with 10% buffered formalin via right ventricle. The lung was inflated by injection of 10% formalin through the trachea. Various organs were excised from the rat and fixed for additional twenty four hours and processed for immunohistochemistory.

Immunohistochemistry

Figure 2:
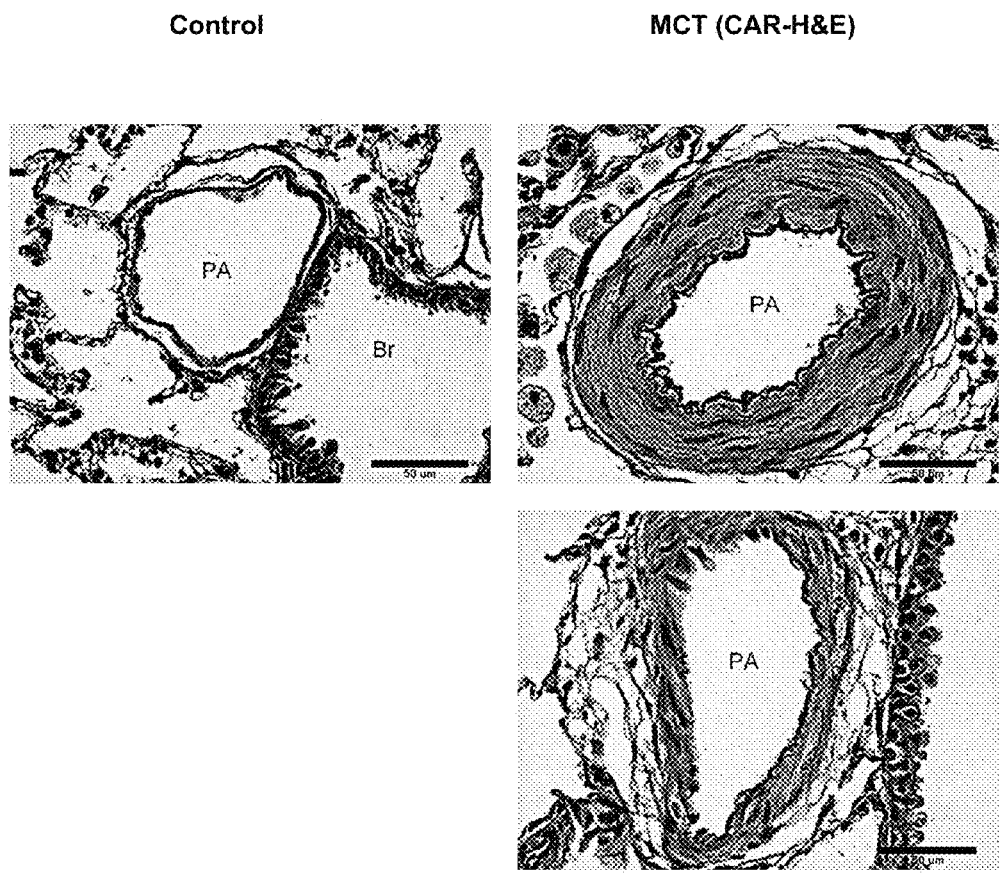
Figure 3:
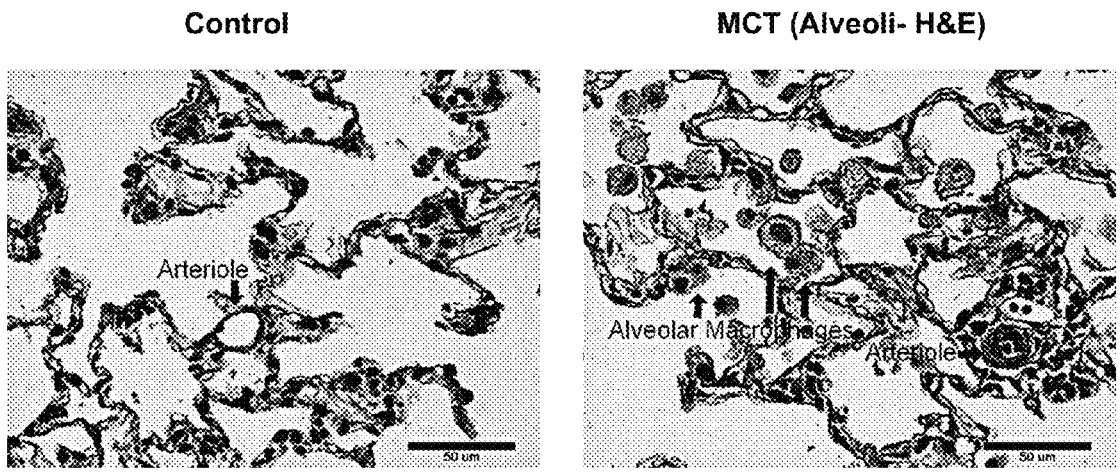
Figure 4:
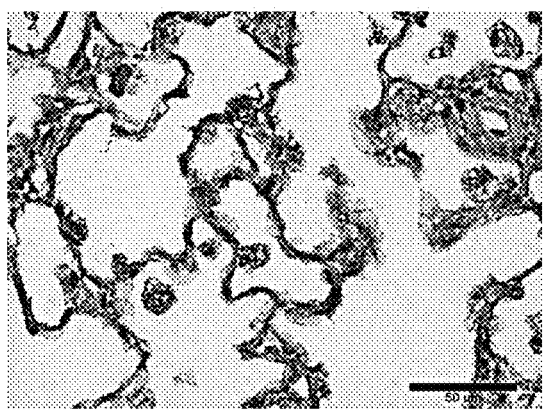
Figure 5:
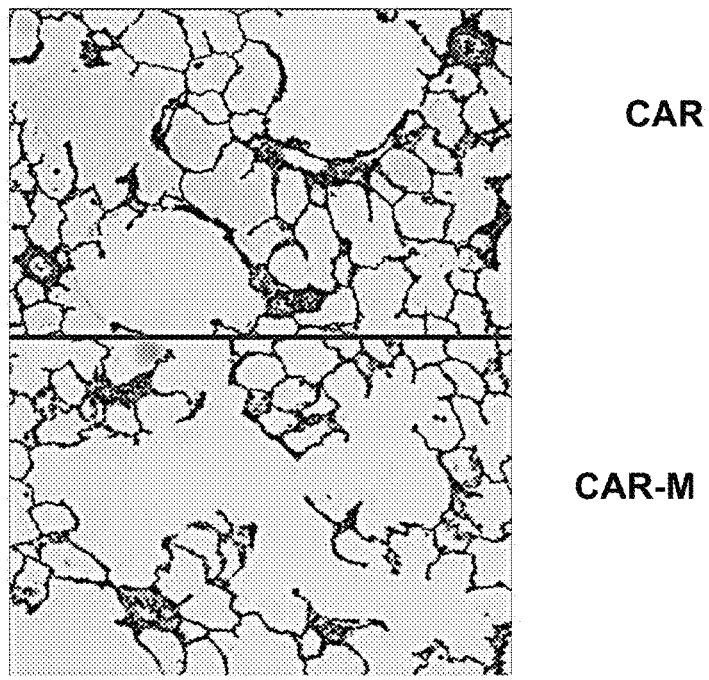
Figure 6:
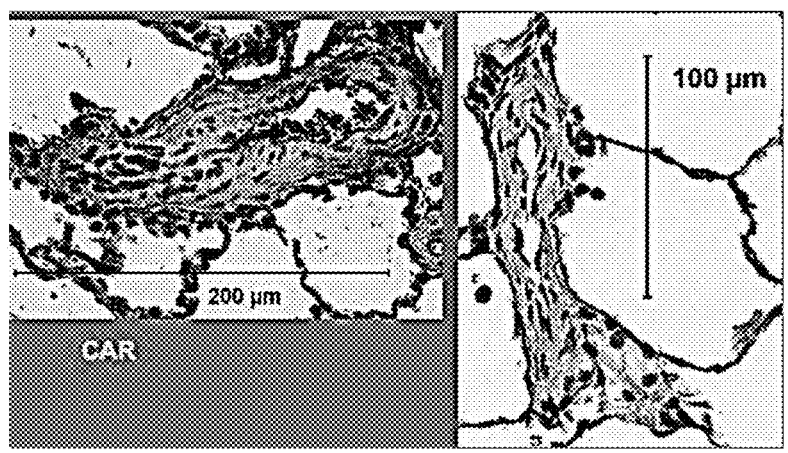
Figure 7:
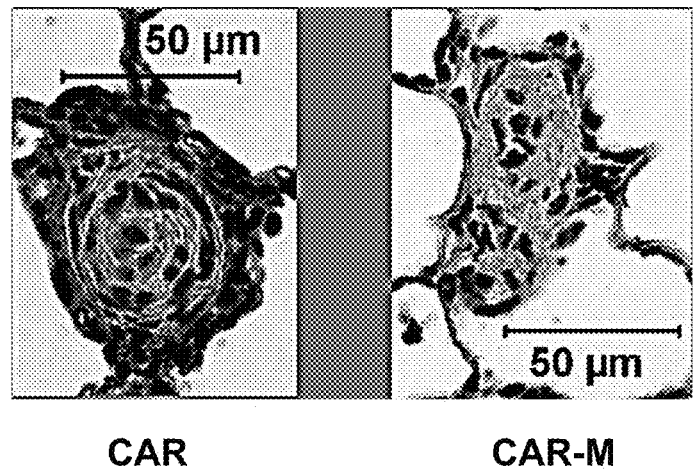
Figure 8:
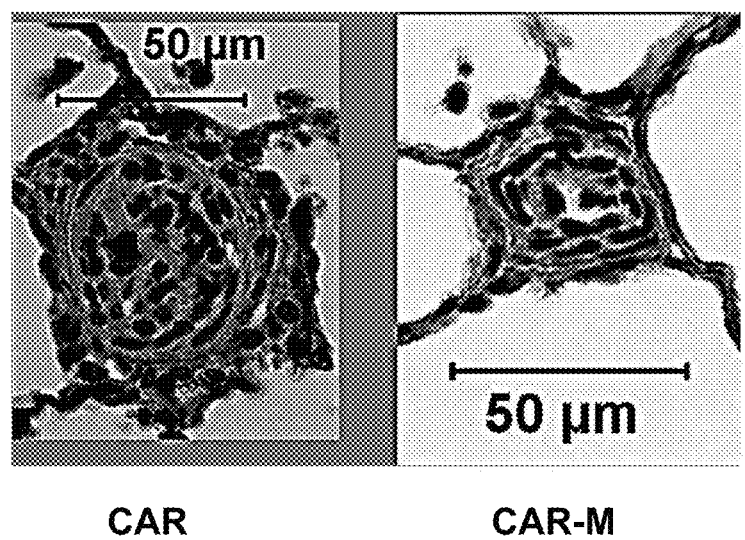
Figure 9:
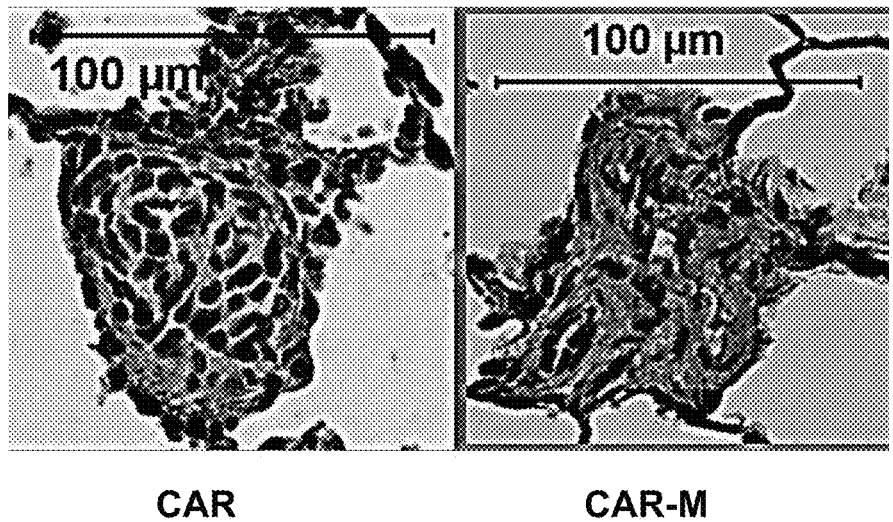
Figure 10:
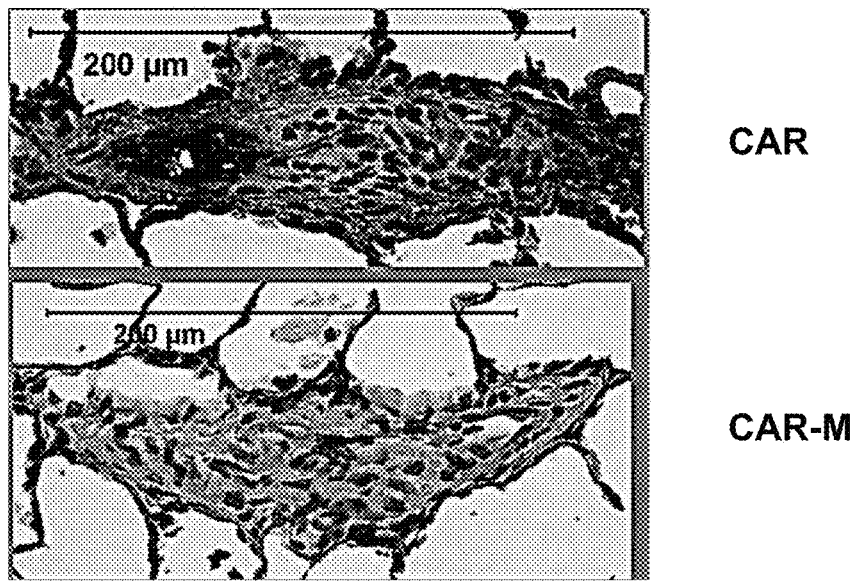
Figure 11:
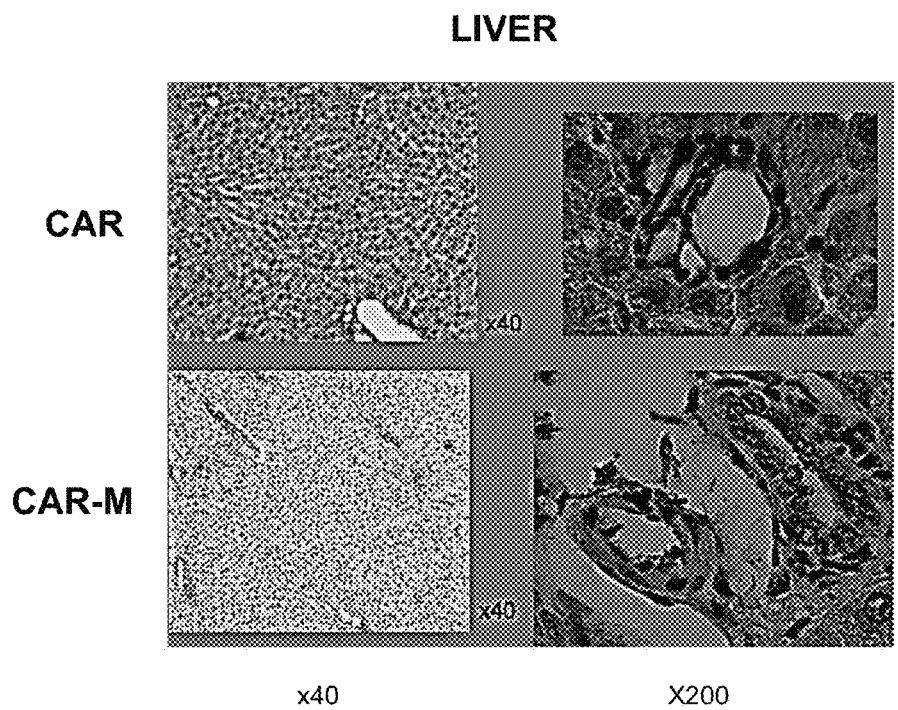
Figure 12:
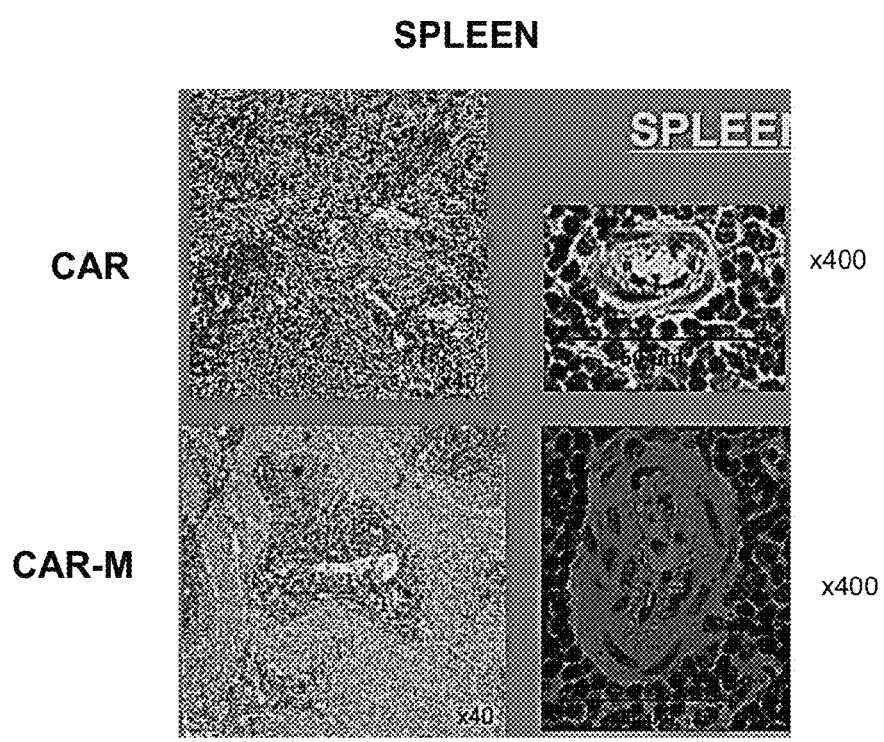
Figure 13:
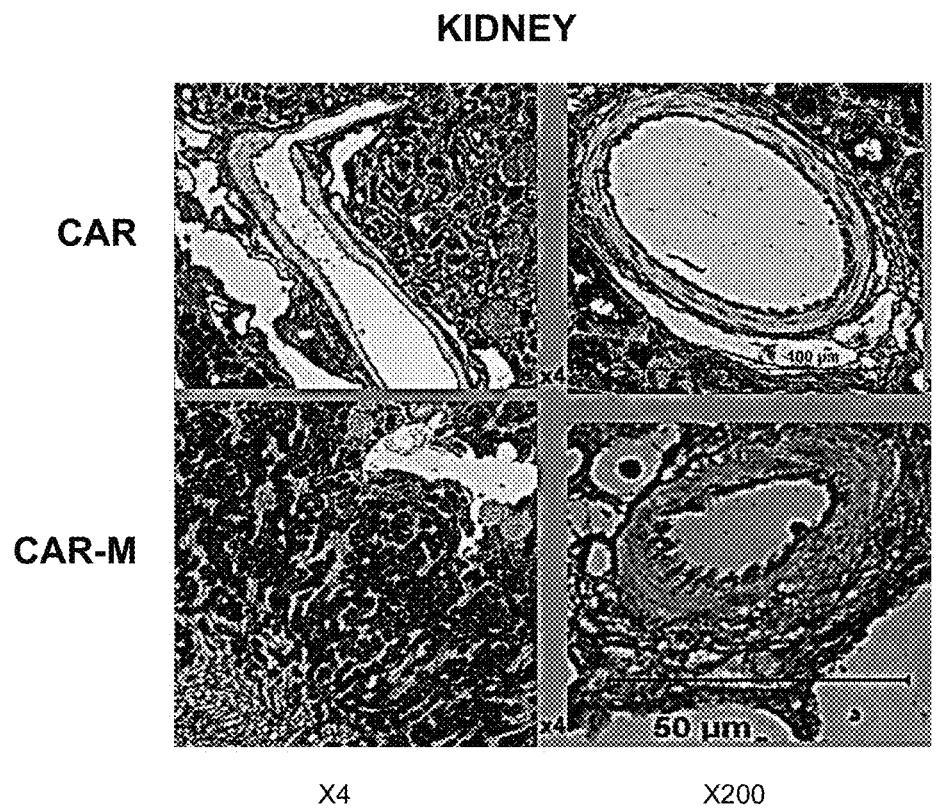
Figure 14:
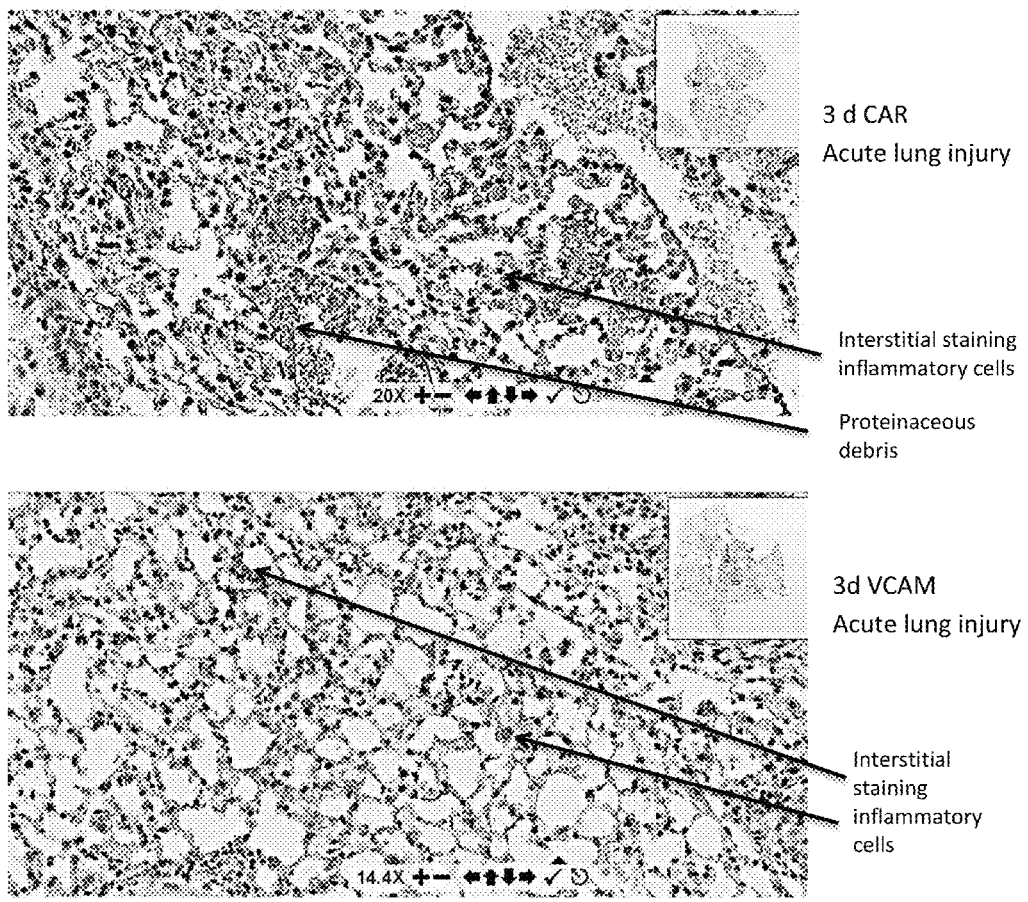
FIG. 14 shows a distribution of CAR and VCAM1 staining in mouse lungs 3 days after bleomycin injection in acute lung injury model. Both CAR and VCAM1 stain the interstitium and inflammatory cells although CAR staining appears to be more intense.
Figure 15:
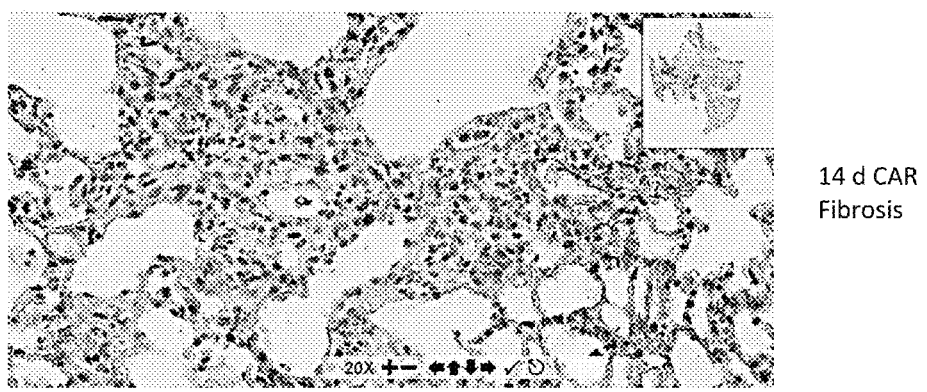
FIG. 15 shows a distribution of CAR staining 14 days after bleomycin injection in pulmonary fibrosis model. Interstitial and inflammatory staining is seen in areas of lung fibrosis.
Figure 15:
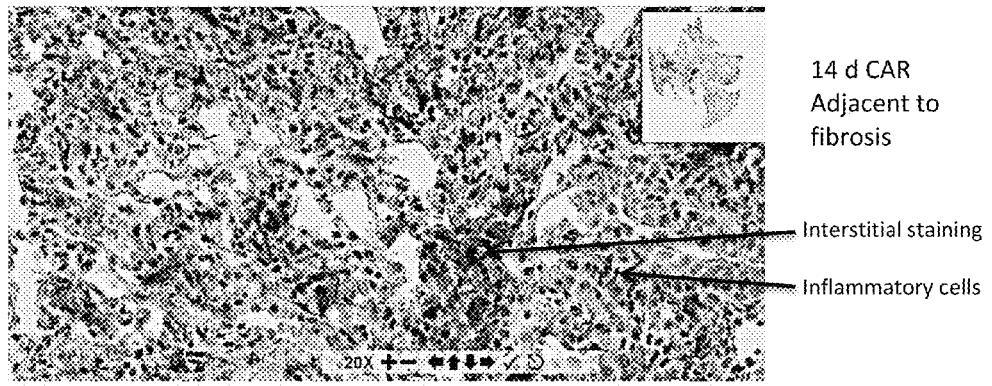
Figure 16:
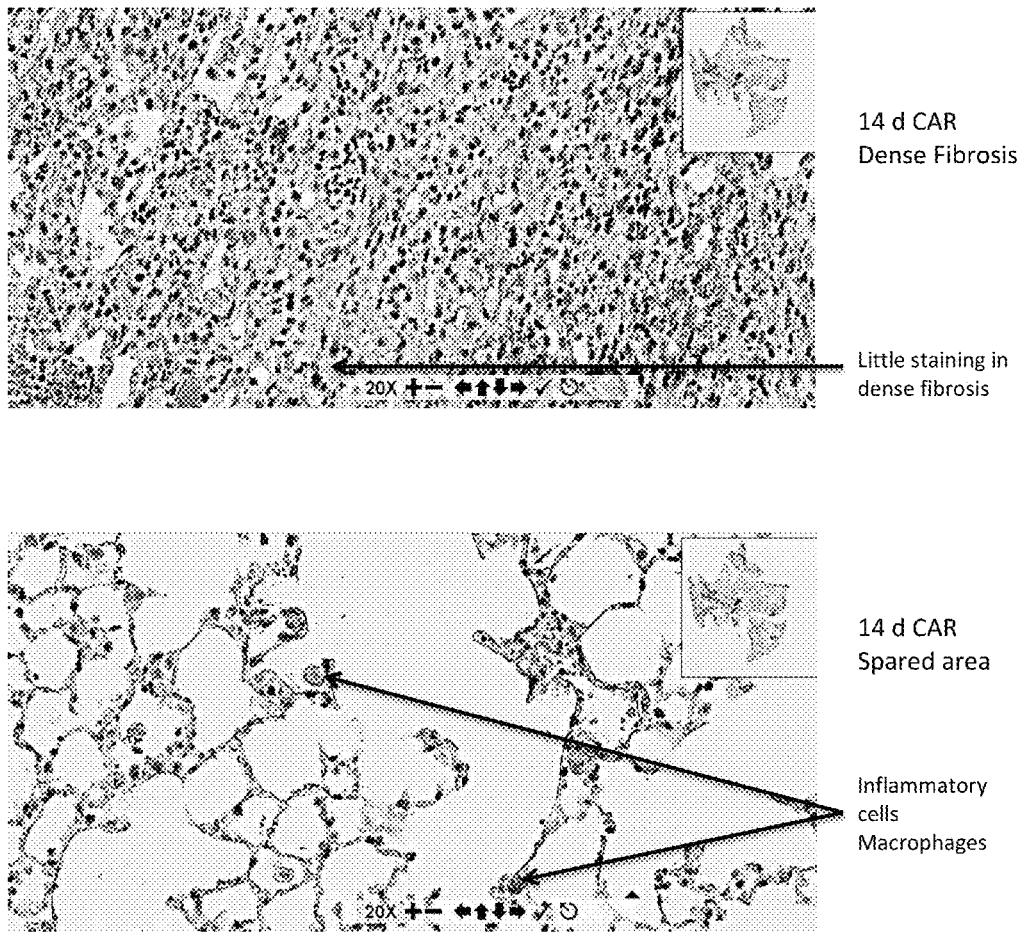
FIG. 16 shows a distribution of CAR staining 14 days after bleomycin injection in areas of dense fibrosis and spared areas showing little staining.
Figure 17:
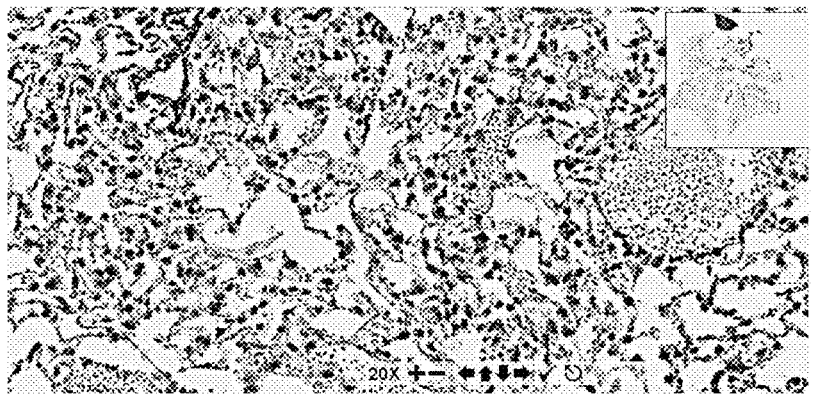
FIG. 17 shows a distribution of VCAM1 staining 14 days after bleomycin injection in areas of mild fibrosis and spared areas showing little staining.
Figure 17:
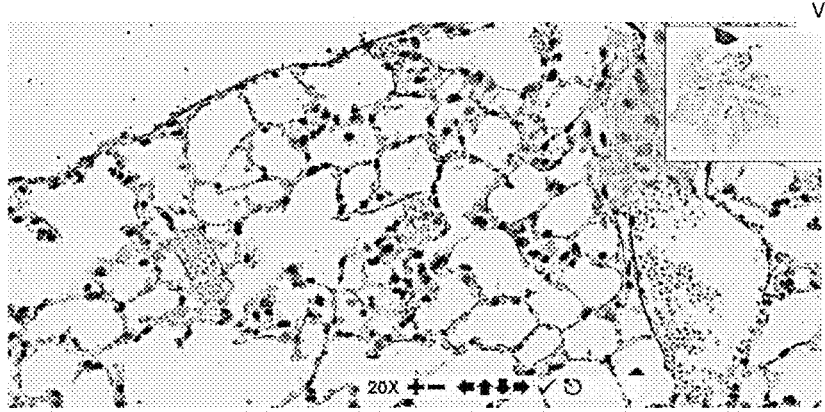

To determine the localization of the peptides, paraffin-embedded tissue sections were immunostained with either hematoxylin and eosin (FIGS. 2-3) or rabbit anti-fluoroscein isothiocyanate (FITC) antibody (Invitrogen, CA) followed by horseradish peroxidase-labeled anti-rabbit IgG secondary antibody (FIG. 4). The peptide localization was then visualized by diaminobenzidine (DAB). An automated staining system, Discovery XT (Ventana, Ariz.) was used. To quantify the targeting efficiency of the peptides to the lung, the immunostained sections were scanned by Aperio Scanscope XT and analyzed using ImageScope software (Aperio Technologies, CA).

II. Targeted Vasodilation in SU5416/Hypoxia/Normoxia-Exposed Severe Occlusive Pulmonary Hypertension Animal Model Adult male Sprague-Dawley rats weighing approximately 200 g are injected subcutaneously with SU5416 (20 mg/kg; SUGEN Inc), which is suspended in carboxymethylcellulose (0.5% [wt/vol]carboxymethylcellulose sodium, 0.9% [wt/vol] NaCl, 0.4% [vol/vol] polysorbate, 0.9% [vol/vol] benzyl alcohol in deionized water). The rats are then exposed to chronic hypoxia in a hypobaric chamber (10% $O_2$) for 3 weeks and are returned to normoxia (21% $O_2$) for an additional 2 to 10 weeks.

Catheterized Rats

Rats are anesthetized with intramuscular pentobarbital sodium (30 mg/kg). The rats are placed on controlled heating pads. Hemodynamic measurements are performed in anesthetized animals under normoxic conditions. Polyvinyl catheters (PV-1, internal diameter: 0.28 mm) are inserted into the right jugular vein for measurement of right ventricular systolic pressure (RVSP) and into the left jugular vein for drug administration. A microtip P-V catheter (SPR-838, Millar Instruments) is inserted into the right carotid artery and advanced into the left ventrical (LV). The signals are continuously recorded by MPVS-300 system with PowerLab/4SP, A/D converter (AD Instruments), and a personal computer. RVSP, heart rate, maximal left ventricular systolic pressure, left ventricular end-diastolic pressure (LVEDP), mean arterial pressure (MAP), cardiac output, and stroke volume are measured. If the heart rate falls below 300 beats/min, the measurements are excluded from analysis. At the end of each hemodynamic study, the rat is sacrificed by an overdose of pentobarbital sodium, and organs are removed for various measurements and analyses.

After baseline hemodynamic measurements, a simple mixture of CAR (1 mg/300 g rat), or control peptide CARM, and fasudil (0.1, 0.3, 1, or 3 mg/kg) or each agent alone is injected intravenously, and all hemodynamic parameters are continuously monitored.

Immunohistochemical Staining

Organs (lung, heart, liver, spleen, and kidney) are collected after blood is flushed with 30 ml phosphate buffered saline (PBS). Lungs are inflated via trachea with 10% formalin at a constant pressure of 20 cm $H_2O$. After 24 hour-fixation with 10% formalin, all organs are embedded in paraffin, and sectioned at 5 mm thickness. After deparaffinization, tissue sections are pretreated with 3% hydrogen peroxidase for 10 minutes and blocked with normal horse serum for 1 hour. They are then incubated for 1 hour with an anti-fluorescein antibody (1:200; Invitrogen) as a primary antibody. After washing with PBS, the sections were incubated with biotinylated secondary antibodies, washed with PBS, and incubated in ABC Regent for 5 minutes. Diaminobenzidine was used as a substrate for the immunoperoxidase reaction. Sections were lightly counterstained with hematoxylin, and analyzed light microscopically (FIGS. 5-13). CAR (but not CARM) was detected in high intensity in all layers of severely remodeled arteries from lung tissue. Neither CAR nor CARM was found in other organs except for the kidney.

III. Bleomycin-Induced Acute Lung Injury and Pulmonary Fibrosis Model

The bleomycin (BL) model is usually considered a model of pulmonary fibrosis, but its administration is also associated with features of acute lung injury (ALI). Bleomycin is an antineoplastic antibiotic drug isolated in 1966 from the actinomycete *Streptomyces verticillus*. Bleomycin forms a complex with oxygen and metals such as $Fe^{2+}$, leading to the production of oxygen radicals, DNA breaks, and ultimately cell death. Bleomycin can be inactivated by bleomycin hydrolase, a cysteine protease that shows variable levels of expression in the lungs. The susceptibility of the lungs to bleomycin-induced toxicity is largely dependent on the levels of expression of bleomycin hydrolase in the lungs; species with high levels of expression, such as rabbits, are relatively resistant to bleomycin-induced toxicity, whereas species with low levels of expression, such as C57BL/6 mice, are sensitive. In addition to species-related differences in bleomycin susceptibility, there are also differences in strain susceptibility, with C57BL/6 mice being highly sensitive.

Animal Model

A mouse model of bleomycin induced acute lung injury and pulmonary fibrosis was used for this study. Briefly, 6 WT C57Bl/6 male mice, 8-12 weeks were weighed and anesthetized, and given bleomycin (BL) intratracheally at 4 U/kg. At 3 days (acute lung injury model) and 14 days (pulmonary fibrosis model) after BL injection, peptides were injected via the tail vein.

Peptides

The following peptides were labeled with 5-carboxyfluorescein (5FAM) and used for the lung targeting studies: CAR, 5FAM-CARSKNKDC; VCAM1, CVHSPNKKCGGSK-5FAM; Control, 5FAM-CGGGGGGGC. All peptides were synthesized by Anaspec (Anaspec Inc., CA). Peptides were resolved in PBS at the concentrations of 0.5 mg/mL.

Peptide Targeting Study

BL-treated mice were injected with peptide solution at a dose of 3.3 mg/kg body weight via the tail vein. At two hours after the injection, mice were perfused with PBS containing 1% bovine serum albumin under the deep anesthesia with isofluorane at a rate of 3.0% and euthanized. Tissues were fixed by systemic perfusion with 10% buffered formalin via right ventricle. The lung was inflated by injection of 10% formalin through the trachea. Various organs were excised from the rat and fixed for additional twenty four hours and processed for immunohistochemistory.

Immunohistochemistry

To determine the localization of the peptides, paraffin-embedded tissue sections were immunostained with rabbit anti-fluoroscein isothiocyanate (FITC) antibody (Invitrogen, CA) followed by horseradish peroxidase-labeled anti-rabbit IgG secondary antibody. The peptide localization was then visualized by diaminobenzidine (DAB). An automated staining system. Discovery XT (Ventana, Ariz.) was used. To quantify the targeting efficiency of the peptides to the lung, the immunostained sections were scanned by Aperio Scanseope XT and analyzed using ImageScope software (Aperio Technologies, CA) (FIGS. 14-17).

Blood Pressure Tracing

Figure 18:
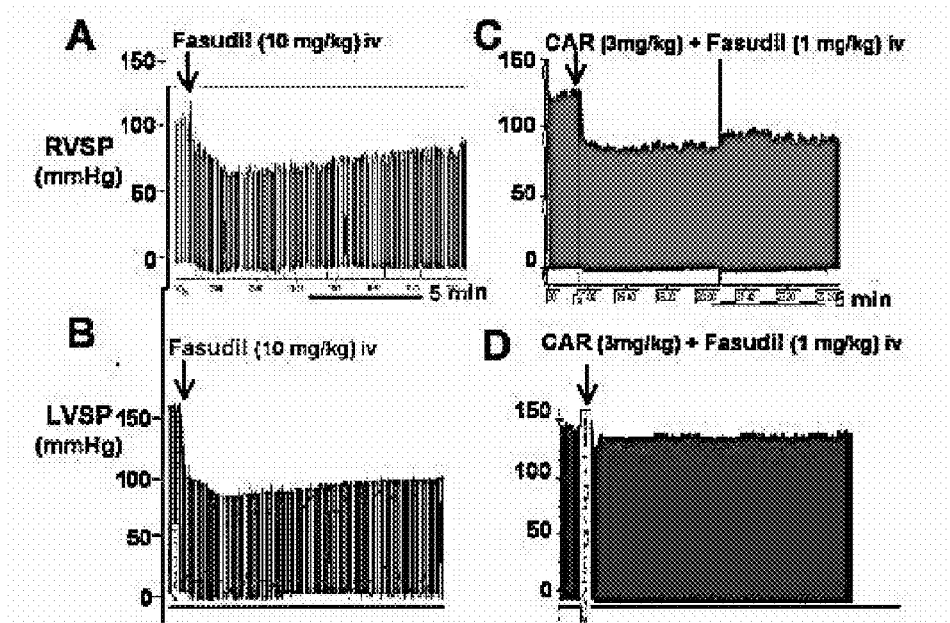
FIG. 18 shows a blood pressure tracing of catheterized SU5416/hypoxia/normoxia-exposed rats with PAH. Acute iv effects of fasudil (10 mg/kg) alone (A and B) and of CAR (1 mg/300 g rat)+fasudil (1 mg/kg) mixture (C and D) on right ventricular (RVSP, A and C) and left ventricular systolic pressure (LVSP, B and D).

To measure the acute effects of fasudil with and without CAR administration on the right and left ventricular systolic pressure, blood pressure measurements were performed on catheterized SU5416/hypoxia/normoxia-exposed rats with PAH (FIGS. 18-19). Surprisingly, co-administered CAR enhanced the blood pressure lowering effect of fasudil on RVSP with only a minor reduction in LVSP, as compared to fasudil alone. Of additional importance, continuous infusion of CAR+fasudil resulted in a sustained, pulmonary-specific effect even after the cessation of the infusion (FIG. 20). An alternative analysis was conducted, observing the same pulmonary-specific effects when comparing pressure in the RVSP to systolic aortic pressure (SAP). While the selective decrease in pulmonary pressure as measured in the RVSP is present, there is no increased CAR effect systemically when co-administered with fasudil (FIG. 21).

IV. CAR Variant+Fasudil Analysis

Animal Model

Severe occlusive PAH rat model was used. Animals were injected with SU5416 (20 mg/kg; SUGEN Inc), followed by 3 weeks hypoxia, then followed by 2-10 weeks normoxia.

Peptides

The peptide administered was a 7 amino acid variant to the CAR peptide used in previous examples. This variant (CARK) consisted of the following sequence: CARSKNK (SEQ ID NO: 2). In these experiments, CARK was administered at a dose of 3 mg/kg and fasudil administered at 1 mg/kg.

Blood Pressure Tracing

To measure the acute effects of fasudil with and CARK administration on the right and left ventricular systolic pressure (or systolic aortic pressure), blood pressure measurements were performed on catheterized SU5w/hypoxia/normoxia-exposed rats with PAH. Similar to CAR, CARK co-administration enhanced the blood pressure lowering effect of fasudil on RVSP with only a minor reduction in SAP (FIG. 22) and LVSP (FIG. 23), as compared to fasudil alone. Interestingly, administration of 10 mg/kg of fasudil 30 minutes after cessation of CARK infusion still resulted in a sustained, pulmonary-specific effect (FIG. 24).

V. CAR+Imatinib Analysis

Animal Model

Severe occlusive PAH rat model was used. Animals were injected with SU5416 (20 mg/kg; SUGEN Inc), followed by 3 weeks hypoxia, then followed by 2-10 weeks normoxia.

Peptides

The peptide administered was CAR, CARSKNKDC (SEQ ID NO: 1). In this experiment, CAR was administered at a dose of 3 mg/kg and imatinib administered at 10 mg/kg.

Blood Pressure Tracing

To measure the acute effects of imatinib with CAR administration on the right and left ventricular systolic pressure, blood pressure measurements were performed on catheterized SU5w/hypoxia/normoxia-exposed rats with PAH. Similar to fasudil, CAR co-administration enhanced the blood pressure lowering effect of imatinib on RVSP with only a minor reduction in LVSP (FIG. 25).

VI. Altered Levels of Gene Expression of Enzymes involved in Heparan Sulfate Proteoglycan Biosynthesis Found in a Progressive Porcine Surgical Shunt Model of PAH Heparan sulfate biosynthetic enzymes are key components in generating a myriad of distinct heparan sulfate structures that carry out multiple biologic activities. To determine whether CAR or any variants utilized the heparan sulfate pathway, an analysis was first performed to identify differential gene expression in the PAH model since CAR displayed both homing and selective therapeutic efficacy in models of PAH.

It was discovered that in the surgical shunt model of PAH, a large increase in gene expression was identified in a select group of genes, all of which are related to the heparan sulfate biosynthetic pathway. The heparan sulfate 2-O-sulfotransferase 1 (HS2ST1) gene, which encodes an enzyme responsible for catalyzing the transfer of sulfate to the C2 position of selected hexuronic acid residues within the maturing heparan sulfate, was found to be greatly increased over time in the PAH pig model (FIG. 26).

Another gene which showed a selective increase in expression in the PAH model was exostosin 1 (EXT1), a glycosyltransferase required for the biosynthesis of heparan sulfate (FIG. 27). Specifically, EXT1 encodes an endoplasmic reticulum-resident type II transmembrane glycosyltranferase involved in the chain elongation step of heparan sulfate biosynthesis.

Other genes identified as exhibiting an increase in expression in the PAH model were glycosyltransferase 8 domain containing 2 (GLT8D2) (FIG. 28), heparan sulfate N-deacetylase/N-sulfotransferase (NDST1) (FIG. 29) and O-linked N-acetylglucosamine transferase (OGT) (FIG. 30).

VII. Peptide Variants

It is possible to modify the sequences disclosed in the present invention by truncation, i.e., SEQ ID NO:2 is a truncated variant of SEQ ID NO:1 in which the terminal 2 amino acids of SEQ ID NO:1 are deleted to produce SEQ ID NO:2.

The conformation of peptide variants can be modeled using molecular and electronic structure modeling programs like MOLDEN.

The molecular and electrostatic potential structure of SEQ ID NO:1 or SEQ ID NO:2 can be modeled, and compared to substitutional variants in which one or more amino acids have been substituted to predict if the variant will have a similar conformation with an expected similar function.

SEQ ID NO:2 was modeled in an energy minimized state and an electrostatic potential map was created to visualize its electrostatic surface. A library of single amino acid substitutional variants of SEQ ID NO:2 were modeled by substituting each of the remaining 19 amino acids for the N terminus cysteine (C) (FIG. 31). The sequences from the library of single amino acid substitutional variants were as follows: AARSKNK (SEQ ID NO:3), NARSKNK (SEQ ID NO:4), SARSKNK (SEQ ID NO:5), TARSKNK (SEQ ID NO:6), MARSKNK (SEQ ID NO:7), GARSKNK (SEQ ID NO:8), VARSKNK (SEQ ID NO:9), LARSKNK (SEQ ID NO:10), IARSKNK (SEQ ID NO:11), HARSKNK (SEQ ID NO:12), FARSKNK (SEQ ID NO:13), WARSKNK (SEQ ID NO:14), YARSKNK (SEQ ID NO:15), QARSKNK (SEQ ID NO:16), EARSKNK (SEQ ID NO:17), DARSKNK (SEQ ID NO:18), RARSKNK (SEQ ID NO:19), KARSKNK (SEQ ID NO:20), PARSKNK (SEQ ID NO:21).

The electrostatic potential conformational structure was compared between SEQ ID NO:2 and each substitutional variant (FIGS. 32-50). Some substitutional variants displayed nearly identical or very similar structures (FIGS. 32-41) indicating a likelihood that substituting the amino acids A, S, M, V, H, T, N, G, L, or I for the N terminus cysteine (C) would result in the substitutional variants AARSKNK (SEQ ID NO:3), SARSKNK (SEQ ID NO:5), MARSKNK (SEQ ID NO:7), VARSKNK (SEQ ID NO:9), HARSKNK (SEQ ID NO:12), TARSKNK (SEQ ID NO:6), NARSKNK (SEQ ID NO:4), GARSKNK (SEQ ID NO:8) and IARSKNK (SEQ ID NO:11) having similar functional characteristics as SEQ ID NO:2. Other substitutional variants showed greater differences in structure compared to CARK (FIGS. 42-50) with predicted different function.

Other substitutional variants can be modeled and predicted in a similar fashion for SEQ ID NO:1 or SEQ ID NO:2 by substituting any of the remaining 19 amino acids for a particular amino acid in either peptide with any resulting similar conformers predicted to have similar function.

VIII. Dendrimer Variants

Dendrimers are macromolecules having well-defined hyperbranched structures.

Peptide dendrimers are radially branched macromolecules that contain a peptidyl branching core and/or peripheral peptide chains, and they can be divided into three categories. One category consists of "grafted" peptide dendrimers, having peptides only as surface functionalities. The second category is peptide dendrimers that composed entirely of amino acids. The third are dendrimers utilizing amino acids in the branching core and surface functional groups, but having non-peptide branching units. Peptide dendrimers can be synthesized using either divergent or convergent approach, and the availability of solid-phase combinatorial methods enables large libraries of peptide dendrimers to be produced and screened for desired properties.

Dendrimer variants of SEQ ID NO:1 or SEQ ID NO:2 can be synthesized. For example, a CARK dendrimer containing 8 CARK residues on a polyamidoamine (PAMAM) core (FIGS. 51-52) can be constructed. Other cores such as Poly (ethylene glycol) can also be used to create dendrimer variants. These dendrimer variants can have dozens, hundreds, or even thousands of CAR or CARK peptide residues on the surface of the dendrimer to provide enhanced functional characteristics. These dendrimers can contain CAR or CARK alone for disease selective homing, cell penetration and delivery of co-administered bioactive agents or contain a bioactive agent within the dendrimer for targeted delivery.

REFERENCES

Aono Y, Nishioka Y, Inayama M, Ugai M, Kishi J, Uehara H, Izumi K, Sone S. Imatinib as a novel antifibrotic agent in bleomycin-induced pulmonary fibrosis in mice. Am J Respir Crit Care Med. 2005 June 1; 171(11):1279-85.

Bishop, J R, Schuksz M, Esko, J D. Heparan sulphate proteoglycans fine-tune mammalian physiology. Nature. Vol 446(26): 1030-37.

Ghofrani H A, Seeger W and Grimminger F. Imatinib for the treatment of pulmonary arterial hypertension. N Engl J. Med. 2005 Sep. 29; 353(13):1412-3.

Gonzalez, P. K., Zhuang, J., Doctrow, S. R., Malfroy, B., Benson, P. F., Menconi, M. J., and Fink, M. P. (1996). Role of oxidant stress in the adult respiratory distress syndrome: evaluation of a novel antioxidant strategy in a porcine model of endotoxin-induced acute lung injury. Shock 6, Suppl 1, S23-6.

Järvinen, T. A. H., and Ruoslahti, E. (in submission). Target-seeking anti-fibrotic compound enhances tissue healing and suppresses scar formation in a wound healing model.

Järvinen, T. A. H., and Ruoslahti, E. (2007). Molecular changes in the vasculature of injured tissues. The American Journal of Pathology, 171(2), 702-711.

Kanthapillai P, Lasserson T J, Walters E H. Sildenafil for pulmonary hypertension. Cochrane Database Syst Rev 2004; 18(4):CD003562

Kuklin, V. N., Kirov, M. Y., Evgenov, O. V., Sovershaev, M. A., Sjoberg, J., Kirova, S. S., and Bjertnaes, L. J. (2004). Novel endothelin receptor antagonist attenuates endotoxin-induced lung injury in sheep. Crit. Care Med., 32: 766-773.

Linhardt, R. J., Cooney, C. L., and Galliher, P. M. (1986). Polysaccharide lyases. Appl. Biochem. Biotechnol. 12:135-177.

Morris, P. E., and Bernard, G. R. (1994). Significance of glutathione in lung disease and implications for therapy. Am J Med. Sci., 307(2), 119-27.

Olschewski, H., Ghofrani, H. A., Walmrath, D., Schermuly, R., Temmesfeld-Wollbruck, B., Grimminger, F., and Seeger, W. (1999). Inhaled prostacyclin and iloprost in severe pulmonary hypertension secondary to lung fibrosis. Am J Respir Crit. Care Med., 160, 600-607.

Pikas D. S., Erikson, I., and Kjellen, L. (2000). Overexpression of different isoforms of glucosaminyl N-deacetylase/N-sulfotransferase results in distinct heparan sulfate N-sulfation patterns. Biochemistry, 39, 4552-4558.

Poon, G. M. K., and Garlepy, J. (2007). Cell-surface proteoglycans as molecular portals for cationic peptide and polymer entry into cells. Biochemical Society Transactions Vol 35, Pt 4, 788-793.

Richter, K., Janicki, S., Jörres, R. A., and Magnussen, H. (2002). Acute protection against exercise-induced bronchoconstriction by formoterol, salmeterol and terbutaline. Eur Respir. 1, 19, 865-871.

Rosenfeld, W. N., Davis, J. M., Parton, L., Richter, S. E., Price, A., Flaster, E., Kassem, N. (1996). Safety and pharmacokinetics of recombinant human superoxide dismutase administered intratracheally to premature neonates with respiratory distress syndrome. Pediatrics, 97(6 Pt 1), 811-7.

Sinuff T., Cook, D. J., Peterson, J. C., Fuller, H. D. (1999). Development, implementation, and ϵvaluation of a ketoconazole practice guideline for ARDS prophylaxis. J Crit Care., 14, 1-6.

Summerford, C., and Samulski, R. J. (1997). Membrane-Associated Heparan Sulfate Proteoglycan Is a Receptor for Adeno-Associated Virus Type 2 Virions. J. Virol., 72(2), 1438-1445.

Veyssier-Belot, C., and Cacoub, P. (1999). Role of endothelial and smooth muscle cells in the physiopathology and treatment management of pulmonary hypertension. Cardiovasc Res., 44, 274-282.

Welty-Wolf, K. E., Carraway, M. S., Miller, D. L., Ortel, T. L., Ezban, M., Ghio, A. J., Idell, S., and Piantadosi C. A. (2001). Coagulation blockade prevents sepsis-induced respiratory and renal failure in baboons. Am J Respir Crit Care Med., 164, 1988-1996.

Wurdinger T and Costa F F (2007). Molecular therapy in the microRNA era. The Pharmacogenomics Journal (2007) 7, 297-304.

What is claimed is:

1. A composition comprising:
   (a) a targeting peptide comprising the amino acid sequence of SEQ ID NO: 1;
   (b) at least one bioactive agent which conveys a therapeutic benefit to a disease, wherein the at least one bioactive agent is a vasodilator; and
   (c) wherein the targeting peptide is not directly or indirectly conjugated to the at least one bioactive agent.

2. The composition of claim 1, wherein the targeting peptide is synthesized.

* * * * *

UNITED STATES PATENT AND TRADEMARK OFFICE
CERTIFICATE OF CORRECTION

PATENT NO. : 9,180,161 B2
APPLICATION NO. : 13/581457
DATED : November 10, 2015
INVENTOR(S) : Komatsu et al.

It is certified that error appears in the above-identified patent and that said Letters Patent is hereby corrected as shown below:

On the title page, item (75), line 3: the word "Busilton" should read "Buelton".

Signed and Sealed this
Twenty-sixth Day of July, 2016

Michelle K. Lee
*Director of the United States Patent and Trademark Office*

SEQUENCE LISTING

```
<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Cys Ala Arg Ser Lys Asn Lys Asp Cys
1               5

<210> SEQ ID NO 2
<211> LENGTH: 7
<212> TYPE: PRT
<213> ORGANISM: Artificial Sequence
<220> FEATURE:
```

<223> OTHER INFORMATION: Synthesized

<400> SEQUENCE: 2

Cys Ala Arg Ser Lys Asn Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthesized

<400> SEQUENCE: 3

Ala Ala Arg Ser Lys Asn Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthesized

<400> SEQUENCE: 4

Asn Ala Arg Ser Lys Asn Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

Ser Ala Arg Ser Lys Asn Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthesized

<400> SEQUENCE: 6

Thr Ala Arg Ser Lys Asn Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthesized

<400> SEQUENCE: 7

Met Ala Arg Ser Lys Asn Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthesized

<400> SEQUENCE: 8

Gly Ala Arg Ser Lys Asn Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthesized

<400> SEQUENCE: 9

Val Ala Arg Ser Lys Asn Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthesized

<400> SEQUENCE: 10

Leu Ala Arg Ser Lys Asn Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthesized

<400> SEQUENCE: 11

Ile Ala Arg Ser Lys Asn Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthesized

<400> SEQUENCE: 12

His Ala Arg Ser Lys Asn Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized

<400> SEQUENCE: 13

Phe Ala Arg Ser Lys Asn Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthesized

```
<400> SEQUENCE: 14

Trp Ala Arg Ser Lys Asn Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthesized

<400> SEQUENCE: 15

Tyr Ala Arg Ser Lys Asn Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthesized

<400> SEQUENCE: 16

Gln Ala Arg Ser Lys Asn Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthesized

<400> SEQUENCE: 17

Glu Ala Arg Ser Lys Asn Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthesized

<400> SEQUENCE: 18

Asp Ala Arg Ser Lys Asn Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthesized

<400> SEQUENCE: 19

Arg Ala Arg Ser Lys Asn Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthesized

<400> SEQUENCE: 20
```

```
Lys Ala Arg Ser Lys Asn Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthesized

<400> SEQUENCE: 21

Pro Ala Arg Ser Lys Asn Lys
1               5
```